United States Patent [19]
Itho et al.
[11] Patent Number: 4,525,356
[45] Date of Patent: Jun. 25, 1985

[54] N-SUBSTITUTED FLAVONE-8-CARBOXAMIDES

[75] Inventors: Yasuo Itho, Katsuyamashi; Hideo Kato, Fukuishi; Nobuo Ogawa, Katsuyamashi; Kagari Yamagishi, Katsuyamashi; Eiichi Koshinaka, Katsuyamashi; Kazuya Mitani, Fukuishi, all of Japan

[73] Assignee: Hokuriku Pharmaceutical Co., Ltd., Katsuyamashi, Japan

[21] Appl. No.: 546,481

[22] Filed: Oct. 28, 1983

[30] Foreign Application Priority Data

| | | | |
|---|---|---|---|
| Nov. 2, 1982 | [JP] | Japan | 57-191803 |
| Feb. 25, 1983 | [JP] | Japan | 58-29409 |
| Apr. 4, 1983 | [JP] | Japan | 58-57868 |
| May 9, 1983 | [JP] | Japan | 58-79343 |
| Jul. 28, 1983 | [JP] | Japan | 58-136735 |

[51] Int. Cl.[3] .................... A61K 31/35; A61K 27/00; C07D 311/30; C07D 405/10

[52] U.S. Cl. .................................... 514/234; 549/403; 548/525; 546/196; 544/151; 514/319; 514/422; 514/456

[58] Field of Search ........................ 549/403; 548/525; 546/196; 544/151; 424/283, 274, 267, 248.54

[56] References Cited

U.S. PATENT DOCUMENTS

| | | | |
|---|---|---|---|
| 2,921,070 | 1/1960 | Da Re | 549/403 |
| 3,002,979 | 10/1961 | Klosa | 549/403 |
| 3,350,411 | 10/1967 | Da Re | 549/403 |

OTHER PUBLICATIONS

Nippon, Chem. Abstr., 100, 191648h, (1983).

*Primary Examiner*—Nicky Chan
*Attorney, Agent, or Firm*—Gordon W. Hueschen

[57] ABSTRACT

Derivatives of N-substituted flavone-8-carboxamides represented by general formula (I)

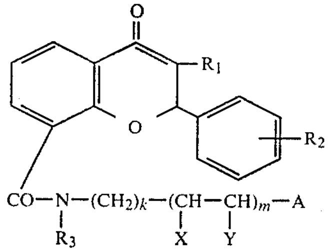

wherein $R_1$ represents a hydrogen atom, a methyl group or an ethyl group, $R_2$ represents a hydrogen atom, a lower alkyl group, a lower alkoxyl group, a halogen atom or a nitro group, $R_3$ represents a hydrogen atom or a lower alkyl group, k represents 0, 1, 2, or 3, m represents 0 or 1; X and Y, which must be different, represent a hydrogen atom or methyl group. A represents an amino group having the formula

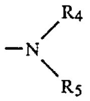

or

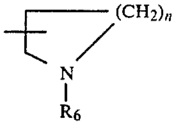

wherein, $R_4$ and $R_5$, which may be the same or different, represent a lower alkyl group or a cyclic amino group together with the nitrogen atom and with or without an oxygen atom, $R_6$ represents a lower alkyl group and n represents 2 or 3, are disclosed, as well as pharmaceutical compositions thereof and method of treating therewith.

The N-substituted flavone-8-carboxamides derivatives are useful as agents for treatment of dysurea.

18 Claims, No Drawings

N-SUBSTITUTED FLAVONE-8-CARBOXAMIDES

BACKGROUND OF THE INVENTION

1. Field of the Invention

The present invention relates to novel derivatives of N-substituted flavone-8-carboxamides represented by the formula (I):

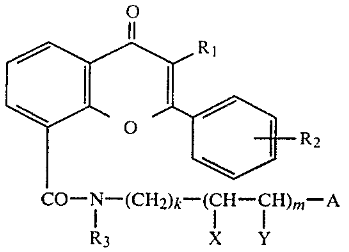

(I)

wherein $R_1$ represents a hydrogen atom, a methyl group or an ethyl group; $R_2$ represents a hydrogen atom, a lower alkyl group, a lower alkoxy group, a halogen atom or a nitro group; $R_3$ represents a hydrogen atom or a lower alkyl group; k represents 0, 1, 2, or 3; m represents 0 or 1, X and Y, which must be different, represent a hydrogen atom or a methyl group; A represents an amino group having the formula

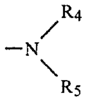 or 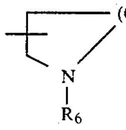

wherein $R_4$ and $R_5$, which may be the same or different, represent a lower alkyl group or a cyclic amino group together with the nitrogen atom and with or without an oxygen atom; $R_6$ represents a lower alkyl group and n represents 2 or 3; which have an excellent effect for removing the impediments to urination (dysuria), non-toxic pharmaceutically-acceptable salts thereof, and process for preparation thereof.

The present invention also relates to pharmaceutical compositions containing the derivatives of the formula (I) and further to a method of treating a patient having an impediment to urination therewith.

2. Description of the Prior Art

As no therapeutical agent having a specific effect for removing impediments to micturition has been known, it has been necessary hitherto to employ, for purposes of eliminating impediments to urination, the available anti-spasmodics or tranquilizers. Recently it has been found that Flavoxate, of the chemical formula (II);

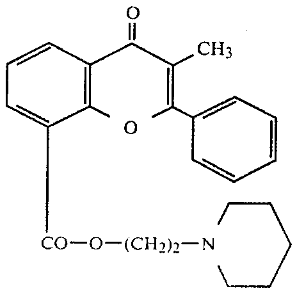

(II)

possesses an activity for treatment of dysuria in practice (Merck Index, 9th Edition, 4012; U.S. Pat. No. 2,921,070). The compound of the prior are is, however, unsatisfactory for clinical use because of its poor effect and lower stability. The compound administrated per os is hydrolyzed in the digestive tract to a less active free carboxylic acid having the formula (III);

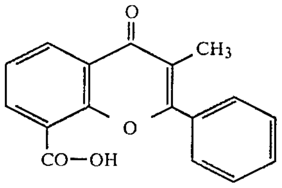

(III)

SUMMARY OF THE INVENTION

An object of the present invention is to provide a satisfactory therapeutic agent, having a high order of activity for eliminating impediments to micturition, and also having sufficient stability so that it may be used as a medicine with extremely favorable results.

A further object of the present invention is to provide a therapeutic composition containing compounds of formula (I), and a method of treating a patient having an impediment to urination therewith.

DETAILED DESCRIPTION OF THE INVENTION

In more detail, the lower alkyl groups represented by $R_2$ and $R_3$ in the formula (I) may be, for example, methyl, ethyl, propyl, isopropyl, butyl, isobutyl, or tert-butyl; the lower alkoxyl group which $R_2$ represents, is, for example, methoxyl, ethoxyl, propoxyl, isopropoxyl or butoxyl, and halogen atoms represents, for example, fluorine, chlorine or bromine. The amino group of the formula

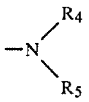

in the formula (I) represents, for example, dimethylamino, diethylamino, dipropylamino, dibutylamino, methylbutylamino, pyrrolidino, piperidino, or morpholino, and the amino group of the formula

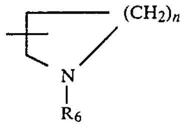

represents, for example, 1-methyl-2-pyrrolidyl, 1-ethyl-2-pyrrolidyl, 1-butyl-2-pyrrolidyl, 1-methyl-3-pyrrolidyl, 1-ethyl-3-pyrrolidyl, 1-butyl-3-pyrrolidyl, 1-methyl-2-piperidyl, 1-ethyl-2-piperidyl, 1-butyl-2-piperidyl, 1-methyl-3-piperidyl, 1-ethyl-3-piperidyl, 1-butyl-3-piperidyl, 1-methyl-4-piperidyl, 1-ethyl-4-piperidyl, or 1-butyl-4-piperidyl. If necessary, the compounds of the present invention represented by formula (I) can be converted into pharmaceutically-acceptable acid addition salts in a conventional manner and the acid addition salts can also be converted into the free base in known manner.

The pharmaceutically-acceptable acid addition salts are, for example, the inorganic acid addition salts such as hydrochloride, hydrobromide hydroiodide, nitrate, sulfate, or phosphate, and the organic acid addition salts such as acetate, maleate, fumarate, citrate, oxalate, or tartarate.

The novel derivatives of N-substituted flavone-8-carboxamide of the formula (I) can be prepared by reaction of a derivative of flavone-8-carboxylic acid of the formula (IV):

(IV)

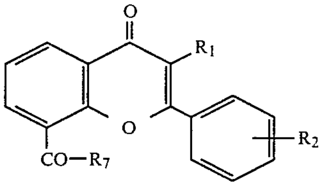

wherein $R_1$ and $R_2$ have the same meanings as defined above, $R_7$ represents a hydroxyl group, a halogen atom, a group of formula O—$R_8$ or O—CO—$OR_9$, wherein each of $R_8$ and $R_9$ represent a lower alkyl group, with a diamine derivative of the formula (V):

(V)

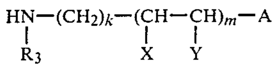

wherein $R_3$, k, m, X, Y and A have the same meanings as defined above.

According to a first embodiment for preparation of the compounds of the present invention, a derivative of flavone-8-carboxylic acid of the formula (IV-1);

(IV-1)

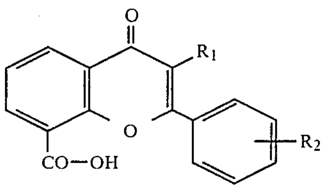

wherein $R_1$ and $R_2$ have the same meanings as defined above, is reacted with a diamine derivative of the formula (V) in an inert organic solvent in the presence of a condensing agent. The condensing agent to be used in the preparation of the present invention is, for example, a carbodiimide such as N,N'-dicyclohexylcarbodiimide, N-cyclohexyl-N'-morpholinoethylcarbodiimide, or N-cyclohexyl-N'-(4-diethylaminocyclohexyl)carbodiimide, or a phosphorus halogenide such as phosphorus trichloride, phosphorus oxychloride, diethylchlorophosphite, o-phenylenechlorophosphite, ethylenedichlorophosphite, or phosphoric anhydride.

The inert organic solvents to be used are, for example, acetone, dioxane, acetonitrile, chloroform, methylene chloride, or tetrahydrofuran.

The reaction is performed at −10° C. to the boiling point of the solvent used (e.g., reflux temperature), preferably at room temperature.

The derivatives of flavone-8-carboxylic acid of formula (IV-1), wherein $R_2$ is a hydrogen atom are known compounds and can be prepared in a conventional manner (Chemische Berichte 99, 1962 (1966)). The flavone-8-carboxylic acid of the formula (IV-1), wherein $R_2$ is a lower alkyl group, a lower alkoxy group, a halogen atom, or a nitro group are new compounds and can be prepared by the following schemes.

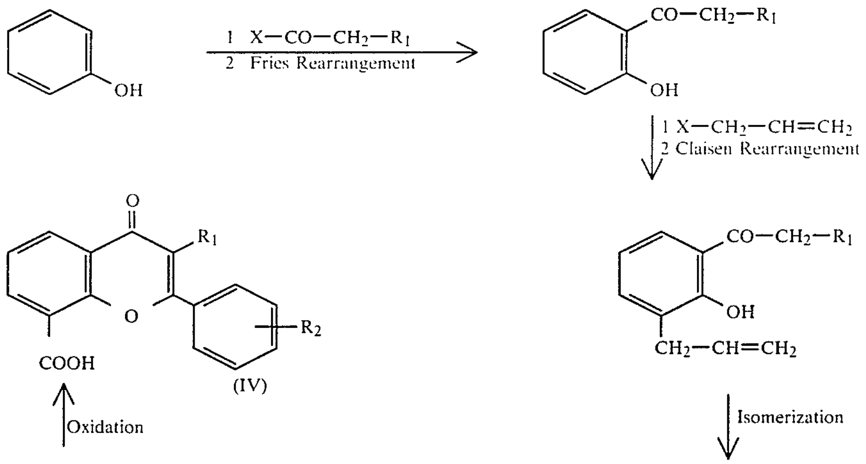

(IV)

-continued

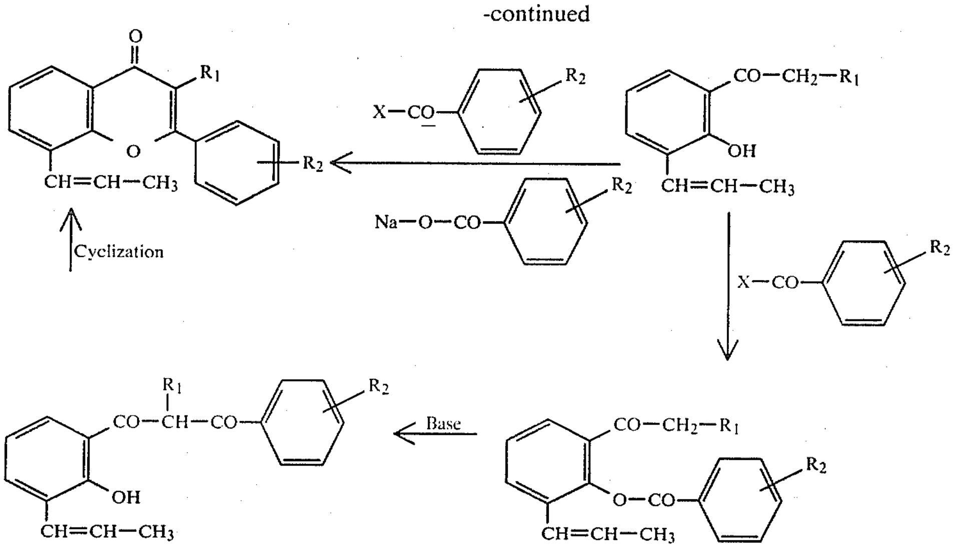

wherein $R_1$ has the same meanings as defined above, $R_2$ represents a lower alkyl group, a lower alkoxyl group, a halogen atom, or a nitro group, and X represents a halogen atom.

Diamine derivatives of the formula (V) are known compounds and can be prepared by a conventional manner, for example, in accordance with the following literature:

Journal of the American Chemical Society 72, 3004 (1950); 68, 100 (1946); 68, 1607 (1946); 66, 725 (1944); 65, 2012 (1943); Helvetica Chimica Acta 26, 1172 (1943); Shionogi Kenkyusho Nempo 10, 1, (1960); Yakugaku Zasshi 62, 224 (1942); 68, 221 (1948); 75, 153 (1955); 81, 149 (1961), Japanese Patent Publication No. 14097 (1972).

According to a second embodiment for the preparation of the compounds of the present invention, a derivative of flavone-8-carboxylic acid halongenide of the formula (IV-2);

(IV-2)

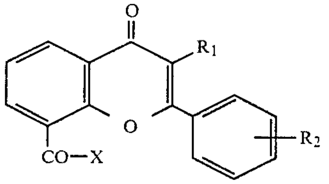

wherein $R_1$ and $R_2$ have the same meanings as defined above, and X represents a halogen atom, is reacted with a diamine derivative of the formula (V) in an inert organic solvent.

As the inert organic solvent can be used any solvents which do not inhibit the reaction, for example, acetone, ether, tetrahydrofuran, dioxane, benzene, toluene, or chloroform.

The reaction is performed at room temperature to the reflux temperature of the solvent used, preferably at room temperature.

The flavone-8-carboxylic acid halogenide derivative of the formula (IV-2) can be prepared from flavone-8-carboxylic acid derivatives of the formula (IV-1) in conventional manner.

According to a third embodiment for the preparation of compounds of the present invention, an ester derivative of flavone-8-carboxylic acid of the formula (IV-3);

(IV-3)

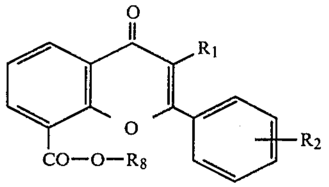

wherein $R_1$ and $R_2$ have the same meanings as defined above, and $R_8$ represents a lower alkyl group, is reacted with a diamine derivative of the formula (V) in an inert organic solvent.

As the inert organic solvent can be used any solvents which do not inhibit the reaction, for example, lower alcohols such as methanol or ethanol, aromatic hydrocarbons such as benzene, xylene or toluene, ethers such as ether, dioxane or tetrahydrofuran, or aprotic polar solvents such as dimethylformamide, dimethylsulfoxide or hexamethylphosphoric triamide.

The reaction is performed at room temperature to the reflux temperature of the solvent used, preferably at the reflux temperature of the solvent.

The ester derivatives of flavone-8-carboxylic acid of the formula (IV-3) are novel compounds excepting the compounds of the formula (IV-3), whereing $R_2$ represents a hydrogen atom and $R_8$ represents methyl or ethyl (Chemische Berichte 99, 1962 (1966); DOS No. 2051269) and can be prepared by the reaction of a flavone-8-carboxylic acid halogenide of the formula (IV-20 with a lower alkanol of the formula (VI)

$$R_8\text{—OH} \qquad \text{(VI)}$$

wherein $R_8$ has the same meaning as defined above.

According to a fourth embodiment for preparation of compounds of the present invention, the mixed anhydride derivative of the flavone-8-carboxylic acid of the formula (IV-4)

(IV-4)

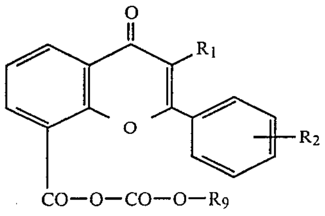

wherein $R_1$ and $R_2$ have the same meanings as defined above and $R_9$ represents a lower alkyl group, is reacted with a diamine derivative of the formula (V) in an inert organic solvent.

As the inert organic solvent can be used any solvents which do not inhibit the reaction, for example, ketones such as acetone, an aromatic hydrocarbon such as benzene or toluene, ethers such as ether, dioxane or tetrahydrofuran, halogenated hydrocarbons such as chloroform or methylene chloride, or aprotic polar solvents, such as dimethylformamide or hexamethylphosphoric triamide.

The reaction is performed at $-10°$ C. to the reflux temperature of the solvent used, preferably at or about roam temperature. The mixed anhydride derivative of flavone-8-carboxylic acid of the formula (IV-4) can be prepared by the reaction of an alkyl halogenocarbonate of the formula (VII);

$$X—CO—O—R_9 \qquad \text{(VII)}$$

wherein $R_9$ has the same meanings as defined above, and X represents a halogen atom, with the flavone-8-carboxylic acid derivative of the formula (IV-1) in the presence of triethylamine in a conventional manner.

The thus prepared N-substituted flavone-8-carboxamide derivatives represented by formula (I) and pharmaceutically acceptable acid addition salts thereof exhibit the effect of removing the impediment to micturation, that is, the supression of urinary reflex and contraction of urinary bladder etc., and are extremely useful as medicaments for alleviating the dysurea, such as pollakiuria, caused by neuropathic pollakiuria, chronic prostatitis and chronic cystitis.

As an example showing effective activity in elimination of the hinderance or impediment to micturition of the present compounds, supression of urinary reflex is shown in Table I, and the excellent stability thereof is shown in Table II.

As reference drugs, three medicaments, flavoxate represented by formula (II), which is on the market, an ester derivative (a compound according to U.S. Pat. No. 2,921,070, Example 2) represented by the formula (VIII);

(VIII)

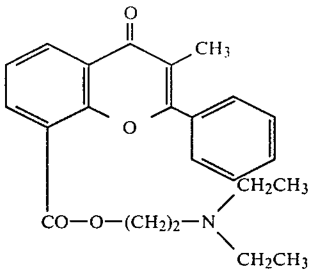

which possesses a structure similar to that of the present compounds, and a free carboxylic acid represented by formula (III), and prepared by hydrolysis thereof, are used.

(Test Compounds)

o Compound of Invention 1 (Example 3)

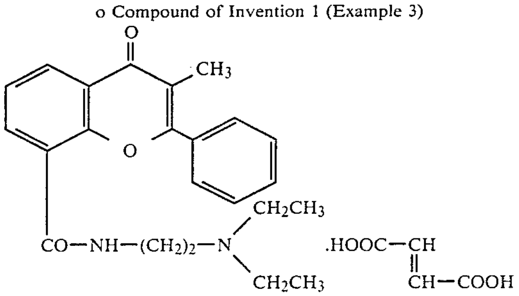

o Compound of Invention 2 (Example 14)

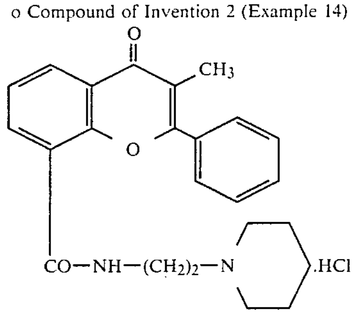

o Compound of Invention 3 (Example 7)

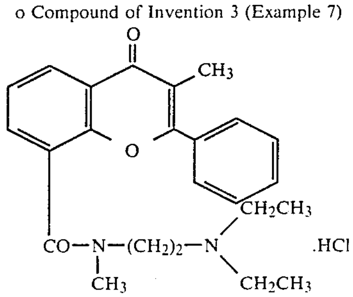

o Compound of Invention 4 (Example 29)

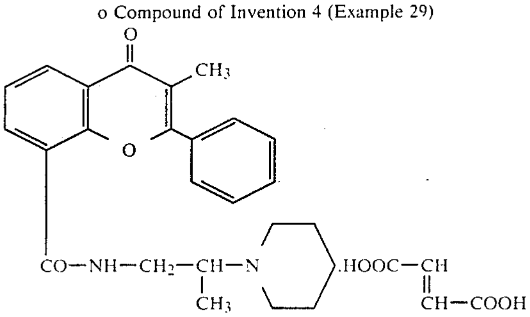

o Compound of Invention 5 (Example 36)

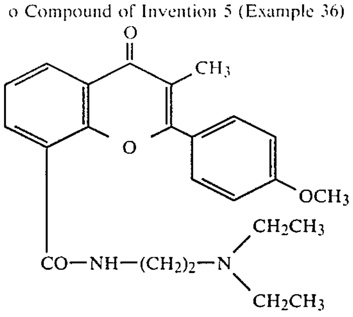

-continued (Test Compounds)

o Reference Drug 1 (flavoxate hydrochloride)

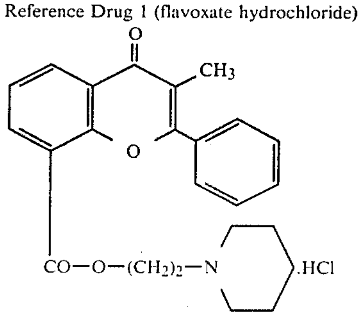

o Reference Drug 2

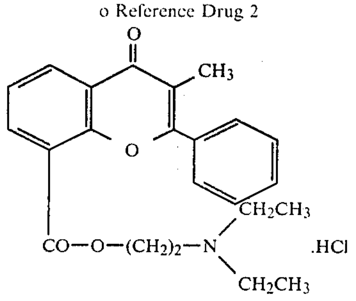

o Reference Drug 3

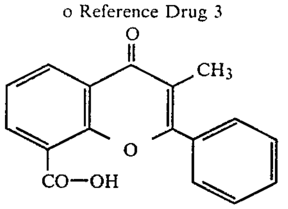

(1) Supression of urinary reflex (Experiment)

According to the method of Kaseda et al. (Rinsho Seiri, 5, 540 (1975)), male Wister rats, weighing approximately 300 g and fasted for 15 to 20 hours prior to experiments, were anesthetized by intraperitoneal injection of 500 mg/Kg of urethane and 50 mg/Kg of $\alpha$-chloralose, and fixed to a supine position. Then the lower abdomen was opened through a midline incision to expose the bladder, and a balloon (1.5 to 2.0 $cm^3$) was inserted into the urinary bladder via small incision in the base thereof. The change of inner pressure is recorded via pressure transducer. The urinary reflex was induced by elevating the inner pressure to 10 to 20 cm $H_2O$. Urine was excreted from the incision of the bladder, where balloon was inserted.

The test compounds were given through polyethylene tube inserted into duodenum via an incision in the fundus.

Mean value of contraction according to the urinary reflex appeared during ten minutes before the administration of the compounds, and at 15, 30, 45 and 60 minutes thereafter, have been investigated for the determination of the effect of the present compounds. The mean value suppressed by more than 50% compared to the initial value has been estimated as effect. $ID_{50}$ (50% effective dose) was obtained by up and down method.

The result as shown in Table 1.

TABLE 1

| | Supression of Urinary Reflex | |
|---|---|---|
| Test Compounds | $ID_{50}$ (mg/Kg) | Ratio of Effect* |
| Compound 1 | 36.7 | 7.42 |
| Compound 2 | 26.8 | 10.16 |
| Compound 3 | 46.7 | 5.83 |
| Compound 4 | 46.7 | 5.83 |
| Compound 5 | 93.3 | 2.92 |
| Reference 1 | 272.3 | 1.00 |
| Reference 2 | 325.1 | 0.84 |
| Reference 3 | 307.6 | 0.89 |

*The Effect of Reference is defined as 1.00

The compounds of the present invention had about 3 to 10 times more potent effect in supressing urinary reflex than Reference drug 1 (flavoxate), which is on the market, as well as Reference drug 2, which possesses a structure similar to the compounds of the present invention.

(2) Stability in acidic medium (corresponding to artificial small intestinal juice)

(Experiment)

After sacrificing male Wister rats (weighing approximately 300 g), small intestine was taken out and small intestinal mucous membrane was scraped off, and 20 ml of 0.1M phosphate buffer (pH 6.00) were added per 0.5 g of small intestinal mucous membrane (wet weight) to give 2.5% of homogenate.

Test compound was dissolved in the homogenate to give definite concentration (50 uM). With shaking of the obtained mixture at 37° C., sampling was carried out from time to time, and the content of each compound was quantitatively measured by analyzing peak height of each compound by a reversed-phase high performance liquid chromatography. The half-life time of each compound in acidic medium (corresponding to artificial small intestinal juice, pH 6.0) was measured from a graph indicating content change of each compound against time.

TABLE 2

| | Half-life Time (T ½) | |
|---|---|---|
| Compounds | T ½ (hr) | Ratio of Effect* |
| Compound 1 | 650.3 | 1066.1 |
| Compound 2 | 290.0 | 475.4 |
| Compound 3 | 153.8 | 252.1 |
| Compound 4 | 778.9 | 1276.9 |
| Compound 5 | 718.2 | 1177.4 |
| Reference 1 | 0.61 | 1.0 |
| Reference 2 | 1.39 | 2.3 |

*Stability of reference 1 is defined as 1.0

The compounds of the present invention and flavoxate (Reference 1) should be absorbed, after p.o. administation, in the small intestine to show medical effect. Therefore, the stability of the compounds against the hydrolyzation according to the nonspecific esterase contained in small intestinal mucous membrane is very important.

The stability of the compounds of the present invention is 110 to 1200 times stronger than for the compounds of References 1 and 2 and excellent as medicament for clinical use.

A compound of the present invention represented by general formula (I) can be administered per os, e.g., in the form of pills or tablets, in which it may be present together with the usual pharmaceutical carriers, conventionally by compounding the compounds of this invention together with a customary carrier or adjuvant, such as talc, magnesium stearate, starch, lactose, gelatin, any of numerous gums, and the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, terra alba, dicalcium acacia, or the like. Representative liquid carriers are peanut oil, sesame oil, olive oil, water, or the like. The active agents of this invention can be conveniently administered in such compositions containing active ingredient so as to eventually be within the dosage range illustrated hereafter. Thus, a wide variety of pharmaceutical forms suitable for many modes of administration and dosages may be employed. For oral administration, the active ingredient and pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion, whereas, for parenteral administration, the composition may be in the form of a sterile solution.

The method of using the compounds of this invention comprises internally or externally administering a compound of this invention, preferably orally or parenterally and preferably admixed with a pharmaceutical carrier, for example, in the form of any of the above compositions, or filled into a capsule, to alleviate conditions to be treated and symptoms thereof in a living animal body. Illustratively, it may be used in an amount of about 50 to about 300 mg. per unit dose, preferably 100 to 200 mg. and 3 times per day for an oral dose and for adult, while parenteral dosages are usually less and ordinarily about one-half of the oral dose. The unit dose is preferably given a suitable number of times daily, typically three times. The daily dose may vary depending upon the number of times given. Naturally, a suitable clinical dose must be adjusted in accordance with the condition, age, and weight of the patient, and it goes without saying that the enhanced activities of the compounds of the invention, together with their reduced side effects, also make them suitable for wide variations, and this invention therefore should not be limited by the exact ranges stated. The exact dosage, both unit dosage and daily dosage, will of course have to be determined according to established medical principles.

The following examples are given by way of illustration only and are not to be construed as limitations of this invention, many variations of which are possible without departing from the scope and spirit thereof.

EXAMPLE 1

N-[2-(N,N'-dimethylamino)]ethyl-3-methylflavone-8-carboxamide

To a solution of 1.53 g of 3-methylflavone-8-carboxylic acid chloride in 60 ml of benzene were added 0.41 g of N,N-dimethylethylenediamine and the solution was refluxed for 2 hours. After cooling, the reaction mixture was extracted with aqueous HCl solution. The water layer was made alkaline with potassium carbonate, and extracted with chloroform. The extract was washed with water, dried, and then evaporated. To the residue, ether was added. The precipitate was filtered to give 0.76 g of colorless crystal, m.p. 133° to 135.5° C. In conventional manner, the compound was changed to fumarate, which was recrystallized from ethanol as colorless needles, m.p. 168° to 170.5° C.

| Elemental analysis for $C_{21}H_{22}N_2O_3.O_4H_4O_4$ | C | H | N |
|---|---|---|---|
| Calcd. (%) | 64.37 | 5.62 | 6.01 |
| Found (%) | 64.48 | 5.70 | 5.96 |

EXAMPLE 2

N-[2-(N',N'-Diethylamino)ethyl]flavone-8-carboxamide

To a solution of 3.20 g of flavone-8-carboxylic acid chloride in 100 ml of benzene were added 1.19 g of N,N-diethylethylenediamine and the solution was refluxed for one hour. After cooling, the precipitate was filtered and dissolved in water. The solution was made alkaline with potassium carbonate, and extracted with chloroform. The extract was washed with water and dried, and then evaporated. To the residue, ether was added. The precipitation was filtered to give 2.25 g of colorless crystals, m.p. 169° to 171° C. In conventional manner, the compound was changed to the fumarate, which was recrystallized from ethanol as colorless needles, m.p. 179.5° to 180.5° C.

| Elemental analysis for $C_{22}H_{24}N_2O_3.C_4H_4O_4$ | C | H | N |
|---|---|---|---|
| Calcd. (%) | 64.99 | 5.87 | 5.83 |
| Found (%) | 65.06 | 5.96 | 5.78 |

EXAMPLE 3

N-[2-(N',N'-Diethylamino)ethyl]-3-methylflavone-8-carboxamide (a) To a solution of 38.72 g of 3-methylflavone-8-carboxylic acid chloride in 500 ml of benzene were added 11.30 g of N,N-diethylethylenediamine and the solution was refluxed for 0.5 hours. The reaction mixture was treated in the same manner as described for Example 2 to give 34.3 g of colorless crystals, which recrystalized from isopropyl ether as a colorless needles, m.p. 105.5° to 108.5° C.

| Elemental analysis for $C_{23}H_{26}N_2O_3$ | C | H | N |
|---|---|---|---|
| Calcd. (%) | 72.99 | 6.92 | 7.40 |
| Found (%) | 72.79 | 7.16 | 7.23 |

In conventional manner, the compound was changed to the fumarate, which was recrystallized from ethanol as colorless plates, m.p. 172.5° to 174.5° C.

| Elemental analysis for $C_{23}H_{26}N_2O_3.C_4H_4O_4$ | C | H | N |
|---|---|---|---|
| Calcd. (%) | 65.58 | 6.11 | 5.66 |
| Found (%) | 65.35 | 6.08 | 5.77 |

(b) To a solution of 1.00 g of ethyl-3-methylflavone-8-carboxylate in 10 ml of ethanol were added 0.55 ml of N,N-diethylethylenediamine and the solution was refluxed for 25.5 hours. The solution was evaporated and the residue was dissolved in aqueous HCl solution and washed with ethyl acetate. The water layer was made alkaline with potassium carbonate and extracted with ethyl acetate. The extract was washed with water, dried and evaporated. To the residue was added isopropyl ether and the precipitate was filtered to give 0.25 g of pale yellow crystals, which were recrystallized from isopropyl ether as colorless needles, m.p. 105.5°–108° C. The compound is identical with the product obtained in Example 3(a) in NMR and IR spectra, and mixed m.p.

(c) To an ice-cooled suspension of 1.00 g of 3-methylflavone-8-carboxylic acid in 20 ml of methylene chloride were added 0.88 g of N,N-dicyclohexylcarbodiimide with stirring, and after 10 minutes also 0.50 ml of N,N-diethylethylenediamine. The mixture was stirred for 1 hour under ice-cooling and then at room temperature for 17 hours. The precipitate was filtrated off and the filtrate was evaporated. The residue was treated in the same manner as described for Example 3(b) to give 0.45 g of colorless crystals, which were recrystallized from isopropyl ether as colorless needles, m.p. 105.5°–108° C. This compound is identical with the product obtained in Example 3(a) in NMR and IR spectra, and mixed m.p.

(d) To an ice-cooled solution of 1.00 g of 3-methylflavone-8-carboxylic and 0.50 ml of triethylamine in 21.5 ml of dry tetrahydrofuran was added a solution of 0.38 ml of ethyl chlorocarbonate in 1 ml of dry tetrahydrofuran and after one hour also a solution of 0.5 ml of N,N-diethyl-ethylenediamine in 1.5 ml of dry tetrahydrofuran. The mixture was stirred for 1.5 hours under ice-cooling and then at room temperature for 16 hours. The precipitate is filtered off and the filtrate was evaporated. The residue was treated in the same manner as described for Example 3(b) to give 0.94 g of colorless crystals, which were recrystallizated from isopropyl ether as colorless needles, m.p. 105.5° to 108° C. This compound was identical with the product obtained in Example 3(a) in NMR and IR spectra, and mixed m.p.

(e) To a solution of 1.00 ml of N,N-diethylethylenediamine in 10 ml of pyridine was added a solution of 0.31 ml of phosphorus trichloride in 2 ml of pyridine under ice-cooling, and the mixture was stirred for 5 minutes under ice-cooling and 1 hour at room temperature. Then to the mixture were added 1.00 g of 3-ethylflavone-8-carboxylic acid and the mixture was strirred for 4.5 hours at 90° to 100° C. The mixture was evaporated and the residue was treated in the same manner as described for Example 3(b) to give 0.65 g of colorless crystals, which were recrystallizated from isopropyl ether as colorless needles, m.p. 105.5° to 108° C. This compound is identical with the product obtained in Example 3(a) in NMR and IR spectra, and mixed m.p.

EXAMPLE 4

N-[(N',N'-Diethylamino)ethyl]-3-ethylflavone-8-carboxamide

To a solution of 3.15 g of 3-ethylflavone-8-carboxylic acid chloride in 100 ml of benzene were added 1.06 g of N,N-diethylethylenediamine and the solution was refluxed for 10 minutes. After cooling, the precipitate was filtered and recrystallized from ethanol to give 3.15 g of the hydrochloride as colorless needles, m.p. 178°–180.5° C.

| Elemental analysis for $C_{24}H_{28}N_2O_3.HCl$ | C | H | N |
|---|---|---|---|
| Calcd. (%) | 67.20 | 6.81 | 6.53 |
| Found (%) | 67.38 | 6.97 | 6.43 |

EXAMPLE 5

N-[3-N',N'-Diethylamino)propyl]-3-methylflavone-8-carboxamide

To a solution of 1.51 g of 3-methylflavone-8-carboxylic acid chloride in 70 ml of benzene were added 0.60 g of N,N-diethyl-1,3-propanediamine and the solution was stirred at room temperature for 0.5 hours. The reaction mixture was extracted with aqueous HCl solution. The water layer was made alkaline with potassium carbonate, and extracted with ethyl acetate. The extract was washed with water, dried, and then evaorated. To the residue, ether was added. The precipitate was filtered to give 0.92 g of pale brown crystals, which were recrystallized from isopropyl ether as colorless needles, m.p. 103° to 104.5° C.

| Elemental analysis for $C_{24}H_{28}N_2O_3$ | C | H | N |
|---|---|---|---|
| Calcd. (%) | 73.44 | 7.19 | 7.14 |
| Found (%) | 73.39 | 7.29 | 7.00 |

EXAMPLE 6

N-[3-(N',N'-Dipropylamino)propyl]-3-ethylflavone-8-carboxamide

To a solution of 1.60 g of 3-ethylflavone-8-carboxylic acid chloride in 60 ml of benzene were added 0.73 g of N,N-dipropyl-1,3-propanediamine and the solution was refluxed for 1.5 hours. The solution mixture was treated in the same manner as described for Example 2, to give 1.25 g of colorless crystals, which were recrystallized from isopropyl ether as colorless needles, m.p. 105.5° to 106° C.

| Elemental analysis for $C_{27}H_{34}N_2O_3$ | C | H | N |
|---|---|---|---|
| Calcd. (%) | 74.62 | 7.89 | 6.45 |
| Found (%) | 74.75 | 8.22 | 6.32 |

EXAMPLE 7

N-[2-(N',N'-Diethylamino)ethyl]-N-methyl-3-methylflavone-8-carboxamide

To a solution of 3.30 g of 3-methylflavone-8-carboxylic acid chloride in 90 ml of benzene were added 1.30 g of N,N-diethyl-N-methylethylenediamine and the solution was stirred at room temperature for one hour. The precipitate was filtered and suspended in 50 ml of water. The suspension was made alkalline with potassium carbonate, and extracted with ethyl acetate. The extract was washed with water, dried, and then evaporated to give 3.66 g of yellow oil.

IR spectrum $\nu$ (film)$cm^{-1}$: 1640 (—CON<, >C=O).

In conventional manner, the compound was converted to the hydrochloride and fumarate.

hydrochloride: colorless plates (from ethanol) m.p. 221.5° to 222° C.

| Elemental analysis for $C_{24}H_{28}N_2O_3.HCl$ | C | H | N |
|---|---|---|---|
| Calcd. (%) | 67.20 | 6.81 | 6.53 |
| Found (%) | 67.09 | 6.88 | 6.35 |

fumarate: colorless plates (from ethanol), m.p. 165.5° to 167.5° C.

| Elemental analysis for $C_{24}H_{28}N_2O_3.C_4H_4O_4$ | C | H | N |
|---|---|---|---|
| Calcd. (%) | 66.13 | 6.34 | 5.51 |
| Found (%) | 65.90 | 6.46 | 5.43 |

EXAMPLE 8

N-[2-(N',Diethylamino)ethyl]-N-methylflavone-8-carboxamide

To a solution of methylflavone-8-carboxylic acid chloride (prepared from 2.00 g of flavone-8-carboxylic acid and 1.1 ml of thionyl chloride) in 50 ml of benzene wre added 0.88 g of N,N-diethyl-N-methylethylenediamine and the mixture was stirred at room temperature for 1.5 hours. The reaction mixture was extracted with aqueous HCl solution. The water layer was made alkaline with potassium carbonate, and extracted with ethyl acetate. The extract was washed with water, dried, and then evaporated to give 2.32 g of a reddish oil.

IR spectrum $\nu$ (film)cm$^{-1}$: 1650 (—CON<, >C=O).

In conventional manner, the compound was converted to the hydrochloride, which was recrystallized from ethanolether to give yellowish brown needles, m.p. 200.5° to 202° C.

| Elemental analysis for $C_{23}H_{26}N_2O_3.HCl$ | C | H | N |
|---|---|---|---|
| Calcd. (%) | 66.58 | 6.56 | 6.75 |
| Found (%) | 66.40 | 6.80 | 6.69 |

EXAMPLE 9

N-[2-(N',N'-diethylamino)ethyl]-N-methyl-3-ethylflavone-8-carboxamide

The mixture of 3-ethylflavone-8-carboxylic acid chloride (prepared from 3.00 g of 3-ethylflavone-8-carboxylic acid and 1.49 ml of thionyl chloride) and 1.19 g of N',N'-diethyl-N-methylethylenediamine were treated in the same manner as in Example 8 to give 3.69 g of reddish brown liquid.

IR spectrum $\nu$ (film)cm$^{-1}$: 1640 (—CON<, >C=O).

In conventional manner, the compound was converted to the fumarate, which was recrystallized from ethanol as colorless plates, m.p. 186°-188.5° C.

| Elemental analysis for $C_{25}H_{30}N_2O_3—C_4H_4O_4$ | C | H | N |
|---|---|---|---|
| Calcd. (%) | 66.65 | 6.56 | 5.36 |
| Found (%) | 66.49 | 6.69 | 5.34 |

EXAMPLE 10

N-[2-(N',N'-dimethylamino)ethyl]-N-methyl-3-methylflavone-8-carboxamide

To a solution of 3.00 g of 3-methylflavone-8-carboxylic acid chloride in 60 ml of benzene were added 0.92 g of N,N-dimethyl-N-methylethylenediamine and the solution was stireed at room temperature for one hour. The precipitate was filtered, and the filtrate was extracted with aqueous HCl solution. To this water layer the obtained precipitate was added and the solution was made alkaline with potassium carbonate and extracted with chloroform. The extract was washed with water, dried, and then evaporated. For the residue, isopropyl ether was added. The precipitate was filtered to give 2.83 g of colorless crystals, m.p. 94°-102° C.

IR spectrum $\nu$ (KBr)cm$^{-1}$: 1650, 1630 (—CON<, >C=O).

In conventional manner, the compound was converted to the fumarate, which was recrystallized from ethanol to give colorless plates, m.p. 214.5° to 216° C.

| Elemental analysis for $C_{22}H_{24}N_2O_3.C_4H_4O_4$ | C | H | N |
|---|---|---|---|
| Calcd. (%) | 64.99 | 5.87 | 5.83 |
| Found (%) | 64.81 | 5.86 | 5.59 |

EXAMPLE 11

N-[2-(N',N'-diethylamino)ethyl]-N-ethyl-3-methylflavone-8-carboxamide

To a solution of 3.00 g of 3-methylflavone-8-carboxylic acid chloride in 65 ml of benzene were added 1.30 g of N,N-diethyl-N-ethylethylenediamine. The mixture was stirred at room temperature for one hour, whereafter the precipitate was filtered. The filtrate was extracted with aqueous HCl solution. The water layer and the obtained precipitate were made alkaline with potassium carbonate and extracted with ethyl acetate. The ethyl acetate layer was washed with water, dried, and then evaporated to give 3.65 g of yellow liquid.

IR spectrum $\nu$ (film)cm$^{-1}$: 1640 (—CON<, >C=O).

In conventional manner, the compound was converted to the hydrochloride and fumarate.

hydrochloride: colorless plates (from ethanol and ether), m.p. 185° to 187° C.

| Elemental analysis for $C_{25}H_{31}N_2O_3.HCl.—H_2O$ | C | H | N |
|---|---|---|---|
| Calcd. (%) | 67.10 | 7.09 | 6.26 |
| Found (%) | 67.11 | 7.20 | 6.02 |

fumarate: colorless plates (from ethanol), m.p. 172° to 175.5° C.

| Elemental analysis for $C_{25}H_{30}N_2O_3.C_4H_4O_4$ | C | H | N |
|---|---|---|---|
| Calcd. (%) | 66.65 | 6.56 | 5.36 |
| Found (%) | 66.73 | 6.63 | 5.36 |

EXAMPLE 12

N-[3-(piperidin-1-yl)propyl]-3-methylflavone-8-carboxamide

To a solution of 1.51 g of 3-methylflavone-8-carboxylic acid chloride in 60 ml of benzene were added 0.65 g of N-(3-aminopropyl)piperidine and the solution was refluxed for 10 minutes. After cooling, the precipitate was filtrated and suspended in water. The suspension was made alkaline with potassium carbonate, and extracted with ethyl acetate. The ethyl acetate layer was washed with water, dried, and the solvent was removed. To the residue ether was added. The precipitate was filtrated to give 0.78 g of colorless crystals, which were recrystallized from isopropyl ether as colorless needles, m.p. 116.5°–117.5° C.

In conventional manner, the compound was converted to the hydrochloride, which was recrystallized from a mixture of ethanol and ether as colorless plates, m.p. 201° to 204° C.

| Elemental analysis for $C_{25}H_{28}N_2O_3 \cdot HCl$ | | | |
|---|---|---|---|
| | C | H | N |
| Calcd. (%) | 68.09 | 6.63 | 6.35 |
| Found (%) | 67.92 | 6.81 | 6.21 |

EXAMPLE 13

N-[2-(piperidin-1-yl)ethyl]flavone-8-carboxamide

To a solution of 3.49 g of flavone-8-carboxylic acid chloride in 80 ml of benzene were added 1.41 g of N-(2-aminoethyl)piperidine and the solution was stirred at room temperature for 1.5 hours. The precipitate was filtered off and added to a mixture of ethyl acetate and aqueous HCl solution, and stirred. The water layer was made alkaline with potassium carbonate, and extracted with ethyl acetate. The ethyl acetate layer was washed with water, dried, and the solvent was removed. To the residue, ether was added. The precipitate was filtrated to give 2.17 g of colorless crystals, which were recrystallized from ethyl acetate as colorless needles, m.p. 162°–165° C.

| Elemental analysis for $C_{23}H_{24}N_2O_3 \cdot \frac{1}{2}H_2O$ | | | |
|---|---|---|---|
| | C | H | N |
| Calcd. (%) | 71.67 | 6.54 | 7.27 |
| Found (%) | 71.47 | 6.67 | 7.03 |

In conventional manner, the compound was converted to the fumarate, which was recrystallized from ethanol as pale yellow needles, m.p. 109.5° to 211° C.

| Elemental analysis for $C_{23}H_{24}N_2O_3 \cdot C_4H_4O_4$ | | | |
|---|---|---|---|
| | C | H | N |
| Calcd. (%) | 65.84 | 5.73 | 5.69 |
| Found (%) | 65.88 | 5.72 | 5.51 |

EXAMPLE 14

N-[2-(piperidin-1-yl)ethyl]-3-methylflavone-8-crboxamide (a) To a solution of 3.30 g of 3-methylflavone-8-carboxylic acid chloride in 90 ml of benzene were added 1.27 g of N-(2-aminoethyl)piperidine and the mixture was stirred at room temperature for 40 minutes. The precipitate was filtered, the filtrate was stirred with aqueous HCl solution, and the precipitate was filtered off. The precipitate was suspended in water together with the previously obtained precipitate and the suspension was made alkaline with potassium carbonate and extracted with chloroform. The chloroform layer was washed with water, dried, and the solvent was evaporated. To the residue ethyl acetate was added and the precipitate was filtered to give 2.94 g of colorless crystals, which were recrystallized from ethyl acetate as colorless needles, m.p. 163°–166° C.

| Elemental analysis for $C_{24}H_{26}N_2O_3$ | | | |
|---|---|---|---|
| | C | H | N |
| Calcd. (%) | 73.82 | 6.71 | 7.17 |
| Found (%) | 73.67 | 6.76 | 7.05 |

In conventional manner, the compound was converted to the hydrochloride and fumarate.

hydrochloride: the colorless needles (from the mixture of ethanol and ether), m.p. 188°–190° C.

| Elemental analysis for $C_{24}H_{26}N_2O_3 \cdot HCl$ | | | |
|---|---|---|---|
| | C | H | N |
| Calcd. (%) | 67.52 | 6.37 | 6.56 |
| Found (%) | 67.36 | 6.44 | 6.33 |

fumarate: colorless needles (from acetone), m.p. 139°–142° C.

| Elemental analysis for $C_{24}H_{26}N_2O_3 \cdot C_4H_4O_4$ | | | |
|---|---|---|---|
| | C | H | N |
| Calcd. (%) | 66.39 | 5.97 | 5.53 |
| Found (%) | 66.43 | 6.00 | 5.45 |

(b) To a solution of 4.00 g of N-(2-aminoethyl)-piperidine in 40 ml of pyridine were added a solution of 1.36 ml of phosphous trichloride in 10 ml of pyridine under ice-cooling and the solution was stirred for 50 minutes at room temperature.

To the obtained solution were added 4.37 g of 3-methylflavone-8-carboxylic acid and the mixture was stirred at a bath temperature of 100° C. for 2.5 hours. The solvent was evaporated and the residue was dissolved in aqueous HCl solution and washed with ethyl acetate. The precipitate and the water layer were made alkaline with potassium carbonate and extracted with chloroform. The chloroform layer was washed with water, dried, and the solvent was evaporated. To the residue was added isopropyl ether and the precipitate was filtered and recrystallized from ethyl acetate to give 2.80 g of colorless needles, m.p. 163°–166° C. This compound was identical with the product obtained in Example 14-(a) in NMR, IR spectra, and mixed m.p.

EXAMPLE 15

N-[2-(piperidin-1-yl)ethyl]-3-ethylflavone-8-carboxamide

To a solution of 3-ethylflavone-8-carboxylic acid chloride (prepared from 3.00 g of 3-ethylflavone-8-carboxylic acid and 2.43 g of thionyl chloride) in 60 ml of benzene were added 1.18 g of N-(2-aminoethyl)piperidine and the solution was stirred at room temperature for 30 minutes. The reaction mixture was treated in the same manner as that described in Example 10 to give 3.44 g of colorless crystals, which were recrystallized from ethyl acetate as colorless needles, m.p. 166°–167° C.

| Elemental analysis for $C_{25}H_{28}N_2O_3$ | | | |
|---|---|---|---|
| | C | H | N |
| Calcd. (%) | 74.23 | 6.98 | 6.93 |
| Found (%) | 74.05 | 7.15 | 6.78 |

In conventional manner the compound was converted to the hydrochloride, which was recrystallized from ethanol as colorless plates, m.p. 200°–202° C.

| Elemental analysis for $C_{25}H_{28}N_2O_3.HCl$ | | | |
|---|---|---|---|
| | C | H | N |
| Calcd. (%) | 68.09 | 6.63 | 6.35 |
| Found (%) | 67.89 | 6.61 | 6.26 |

EXAMPLE 16

N-[2-(pyrrolidin-1-yl)ethyl]-3-methylflavone-8-carboxamide

To a solution of 3-methylflavone-8-carboxylic acid chloride (prepared from 3.00 g of 3-methylflavone-8-carboxylic acid and 3.40 g of thionyl chloride) in 80 ml of benzene were added 1.04 g of N-(2-aminoethyl)pyrrolidine and the solution was refluxed for 10 minutes. After cooling, aqueous HCl solution was added. The precipitate and water layer were made alkaline with potassium carbonate and extracted with ethyl acetate. The extract was washed with water, dried, and evaporated. To the residue was added ether and the precipitate was filtered to give 2.80 g of colorless crystals, m.p. 179.5°–181.5° C.

In conventional manner, the compound was converted to the hydrochloride and fumarate.

hydrochloride: colorless needles (from mixture of ethanol and acetone), m.p. 108.5°–111.5° C.

| Elemental analysis for $C_{23}H_{24}N_2O_3.HCl.H_2O$ | | | |
|---|---|---|---|
| | C | H | N |
| Calcd. (%) | 64.11 | 6.32 | 6.50 |
| Found (%) | 64.18 | 6.39 | 6.28 |

fumarate: colorless prisms (from ethanol) m.p. 163°–165° C.

| Elemental analysis for $C_{23}H_{24}N_2O_3.C_4H_4O_4$ | | | |
|---|---|---|---|
| | C | H | N |
| Calcd. (%) | 65.84 | 5.73 | 5.69 |
| Found (%) | 65.92 | 5.80 | 5.63 |

EXAMPLE 17

N-[2-(morpholin-4-yl)ethyl]-3-methylflavone-8-carboxamide

The same procedure as described for Example 14 was carried out using a solution of 3.00 g of 3-methylflavone-8-carboxylic acid chloride in 80 ml of benzene and 1.18 g of N-(2-aminoethyl)morpholine to give 2.99 g of colorless crystals, which were recrystallized from ethyl acetate as colorless needles, m.p. 198°–201.5° C.

| Elemental analysis for $C_{23}H_{24}N_2O_4.\frac{1}{4}H_2O$ | | | |
|---|---|---|---|
| | C | H | N |
| Calcd. (%) | 69.59 | 6.22 | 7.06 |
| Found (%) | 69.82 | 6.05 | 7.05 |

In conventional manner the compound was converted to the hydrochloride, which was recrystallized from methanol as colorless needles, m.p. 210°–212.5° C.

| Elemental analysis for $C_{23}H_{24}N_2O_4.HCl$ | | | |
|---|---|---|---|
| | C | H | N |
| Calcd. (%) | 64.41 | 5.87 | 6.53 |
| Found (%) | 64.23 | 5.88 | 6.36 |

EXAMPLE 18

N-[3-(pyrrolidin-1-yl)propyl]flavone-8-carboxamide

To a solution of 2.34 g of flavone-8-carboxylic acid chloride in 60 ml of benzene were added 0.95 g of N-(3-aminopropyl)pyrrolidine and the solution was stirred at room temperature for 30 minutes. The reaction mixture was treated in the same manner as described for Example 13, to give 1.48 g of pale brown crystals, which were recrystallized from ethyl acetate as colorless needles, m.p. 166°–169.5° C.

| Elemental analysis for $C_{23}H_{24}N_2O_3.\frac{1}{2}H_2O$ | | | |
|---|---|---|---|
| | C | H | N |
| Calcd. (%) | 71.67 | 6.54 | 7.27 |
| Found (%) | 72.06 | 6.47 | 7.19 |

In conventional manner the compound was converted to the fumarate, which was recrystallized from a mixture of ethanol and acetone as colorless needles, m.p. 141.5°–147° C.

| Elemental analysis for $C_{23}H_{24}N_2O_3.C_4H_4O_4.\frac{1}{2}H_2O$ | | | |
|---|---|---|---|
| | C | H | N |
| Calcd. (%) | 64.66 | 5.83 | 5.59 |
| Found (%) | 64.53 | 5.87 | 5.54 |

EXAMPLE 19

N-[3-(morpholin-4-yl)propyl]-3-methylflavone-8-carboxamide

The same procedure as described for Example 10 was carried out using a solution of 3.00 g of 3-methylflavone-8-carboxylic acid chloride in 60 ml of benzene and 1.30 g of N-(3-aminopropyl)morpholine to give 2.82 g of colorless crystals, which were crystallized from ethyl acetate as colorless needles, m.p. 161.5°–162° C.

| Elemental analysis for $C_{24}H_{26}N_2O_4$ | | | |
|---|---|---|---|
| | C | H | N |
| Calcd. (%) | 70.92 | 6.45 | 6.89 |
| Found (%) | 70.72 | 6.33 | 6.86 |

In conventional manner the compound was converted to the hydrochloride, which was recrystallized from methanol as colorless needles, m.p. 217°-220° C.

| Elemental analysis for $C_{24}H_{26}N_2O_4.HCl$ | C | H | N |
|---|---|---|---|
| Calcd. (%) | 65.08 | 6.14 | 6.32 |
| Found (%) | 64.96 | 6.17 | 6.31 |

EXAMPLE 20

N-(1-Ethylpiperidin-3-yl)-3-methylflavone-8-carboxamide

To a solution of 3.00 g of 3-methylflavone-8-carboxylic acid chloride in 60 ml of benzene were added 1.16 g of 3-amino-1-ethylpiperidine and the solution was stirred at room temperature for 1 hour. The mixture was treated in the same manner as that given for Example 1 to give 3.17 g of colorless crystals, which were recrystallized from ethyl acetate as colorless needles, m.p. 188°-189.5° C.

| Elemental analysis for $C_{24}H_{26}N_2O_3$ | C | H | N |
|---|---|---|---|
| Calcd. (%) | 73.82 | 6.71 | 7.17 |
| Found (%) | 74.10 | 6.78 | 7.19 |

In conventional manner the compound was converted to the hydrochloride and fumarate.

hydrochloride: colorless needles (from acetone), m.p. 141.5°-144° C.

| Elemental analysis for $C_{24}H_{26}N_2O_3.HCl.3/2H_2O$ | C | H | N |
|---|---|---|---|
| Calcd. (%) | 63.50 | 6.66 | 6.17 |
| Found (%) | 63.68 | 6.41 | 6.07 |

fumarate: colorless needles (from methanol), m.p. 212.5-215 (decomp.).

| Elemental analysis for $C_{24}H_{26}N_2O_3.C_4H_4O_4$ | C | H | N |
|---|---|---|---|
| Calcd. (%) | 66.39 | 5.97 | 5.53 |
| Found (%) | 66.35 | 5.96 | 5.46 |

EXAMPLE 21

N-[(1-Ethylpyrrolidin-2-yl)methyl]-3-methylflavone-8-carboxamide

To a solution of 3-methylflavone-8-carboxylic acid chloride (prepared from 4.00 g of 3-methylflavone-8-carboxylic acid and 3.40 g of thionyl chloride) in 90 ml of benzene were added 1.66 g of 2-aminomethyl-1-ethylpyrrolidine and the solution refluxed for 1.5 hours. The reaction mixture was treated in the same manner as that given for Example 16, to yield 4.25 g of colorless crystals, which was recrystallized from isopropyl ether as colorless needles, m.p. 116.5°-118° C.

| Elemental analysis for $C_{24}H_{26}N_2O_3$ | C | H | N |
|---|---|---|---|
| Calcd. (%) | 73.82 | 6.71 | 7.17 |
| Found (%) | 73.51 | 6.73 | 6.98 |

In conventional manner, the compound was converted to the hydrochloride and fumarate.

hydrochloride: colorless needles (from acetone), m.p. 115.5°-117° C.

| Elemental analysis for $C_{24}H_{26}N_2O_3.HCl.5/4H_2O$ | C | H | N |
|---|---|---|---|
| Calcd. (%) | 64.14 | 6.62 | 6.23 |
| Found (%) | 64.23 | 6.68 | 6.08 |

fumarate: pale brown plates (from ethanol, m.p. 181.5°-183.5° C.

| Elemental analysis for $C_{24}H_{26}N_2O_3.C_4H_4O_4$ | C | H | N |
|---|---|---|---|
| Calcd. (%) | 66.37 | 6.16 | 5.43 |
| Found (%) | 66.39 | 5.97 | 5.53 |

EXAMPLE 22

N-[2-(1-Methylpyrrolidin-2-yl)ethyl]-3-methylflavone-8-carboxamide

Using 3.00 g of 3-methylflavone-8-carboxylic acid chloride in 50 ml of benzene and 1.16 g of 2-(2-aminoethyl)-1-methyl pyrrolidine, the same reaction as that mentioned for Example 10 was carried out to give 2.87 g of pale yellow crystals, which were recrystallized from ethyl acetate as pale yellow needles, m.p. 147°-150.5° C.

| Elemental analysis for $C_{24}H_{26}N_2O_3.\frac{1}{4}H_2O$ | C | H | N |
|---|---|---|---|
| Calcd. (%) | 72.98 | 6.76 | 7.09 |
| Found (%) | 72.99 | 6.61 | 6.90 |

In conventional manner, the compound was converted to the fumarate, which was recrystallized from ethanol as pale yellow plates, m.p. 175°-177.5° C.

| Elemental analysis for $C_{24}H_{26}N_2O_3.C_4H_4O_4$ | C | H | N |
|---|---|---|---|
| Calcd. (%) | 66.39 | 5.97 | 5.53 |
| Found (%) | 66.27 | 5.89 | 5.55 |

EXAMPLE 23

N-[2-(1-Methylpyrrolidin-2-yl)ethyl]-3-ethylflavone-8-carboxamide

Using a solution of 3-ethylflavone-8-carboxylic acid chloride (prepared from 3.00 g of 3-ethylflavone-8-carboxylic acid and 2.43 g of thionyl chloride) in 60 ml of benzene and 1.18 g of 2-(2-aminoethyl)-1-methylpyrrolidine, the same procedure was carried out as in Example 10 to give 2.70 g of colorless crystals, which are recrystallized from ethyl acetate as colorless needles, m.p. 163°-165° C.

| Elemental analysis for $C_{25}H_{28}N_2O_3$ | C | H | N |
|---|---|---|---|
| Calcd. (%) | 74.23 | 6.98 | 6.93 |
| Found (%) | 73.95 | 7.05 | 6.82 |

In conventional manner, the compound was converted to the fumarate, which was recrystallized from ethanol as colorless needles, m.p. 164°-166° C.

| Elemental analysis for $C_{25}H_{28}N_2O_3.C_4H_4O_4$ | C | H | N |
|---|---|---|---|
| Calcd. (%) | 66.91 | 6.20 | 5.38 |
| Found (%) | 66.87 | 6.17 | 5.37 |

EXAMPLE 24

N-[(2-Dimethylamino-1-methyl)ethyl]flavone-8-carboxamide

To a solution of flavone-8-carboxylic acid chloride (prepared from 1.00 g of flavone-8-carboxylic acid and 0.90 g of thionyl chloride) in 30 ml of benzene were added 0.35 g of (2-dimethylamino-1-methyl)ethylamine and the mixture stirred at room temperature for 80 minutes. The reaction mixture was treated in the same manner as in Example 1, to give 1.00 g of reddish brown crystals, which were recrystallized from ethyl acetate as colorless needles, m.p. 190.5°-191.5° C.

| Elemental analysis for $C_{21}H_{22}N_2O_3$ | C | H | N |
|---|---|---|---|
| Calcd. (%) | 71.98 | 6.33 | 7.99 |
| Found (%) | 72.15 | 6.46 | 7.98 |

In conventional manner, the compound was converted to the fumarate, which was recrystallized from methanol as pale brown needles, m.p. 196.5°-197.0° C.

| Elemental analysis for $C_{21}H_{22}N_2O_3.C_4H_4O_4$ | C | H | N |
|---|---|---|---|
| Calcd. (%) | 64.39 | 5.62 | 6.01 |
| Found (%) | 64.33 | 5.85 | 5.98 |

EXAMPLE 25

N-[(2-Dimethylamino-1-methyl)ethyl]-3-methylflavone-8-carboxamide

Using a solution of 2.50 g of 3-methylflavone-8-carboxylic acid chloride in 40 ml of benzene and 0.77 g of (2-dimethyl-amino-1-methyl)ethylamine, the same reaction as in Example 1 was performed to give 2.29 g of colorless crystals, which were recrystallized from ethyl acetate as colorless needles, m.p. 148°-151° C.

| Elemental analysis for $C_{22}H_{24}N_2O_3$ | C | H | N |
|---|---|---|---|
| Calcd. (%) | 72.51 | 6.64 | 7.69 |
| Found (%) | 72.75 | 6.82 | 7.69 |

In conventional manner, the compound was converted to the fumarate, which was recrystallized from ethanol as colorless plates, m.p. 182°-183° C.

| Elemental analysis for $C_{22}H_{24}N_2O_3.C_4H_4O_4$ | C | H | N |
|---|---|---|---|
| Calcd. (%) | 64.99 | 5.87 | 5.83 |
| Found (%) | 65.20 | 6.07 | 5.81 |

EXAMPLE 26

N-[(2-Dimethylamino-1-methyl)ethyl]-3-methylflavone-8-carboxamide

The same procedure as in Example 1 was performed using a solution of 3-methylflavone-8-carboxylic acid chloride (prepared from 3.0 g of 3-methylflavone-8-carboxylic acid and 2.56 g of thionyl chloride) in 30 ml of benzene and 1.25 g of (2-diethylamino-1-methyl)ethylamine to give 3.17 g of colorless crystals, which were recrystallized from isopropyl as colorless needles, m.p. 127°-128° C.

| Elemental analysis for $C_{24}H_{28}N_2O_3$ | C | H | N |
|---|---|---|---|
| Calcd. (%) | 73.44 | 7.19 | 7.14 |
| Found (%) | 73.49 | 7.16 | 7.07 |

In conventional manner, the compound was converted to the fumarate, which was recrystallized from ethanol as colorless prisms, m.p. 149.5°-151° C.

| Elemental analysis for $C_{24}H_{28}N_2O_3.C_4H_4O_4$ | C | H | N |
|---|---|---|---|
| Calcd. (%) | 66.13 | 6.34 | 5.51 |
| Found (%) | 65.97 | 6.36 | 5.49 |

EXAMPLE 27

N-[(2-Diethylamino-1-methyl)ethyl]-3-ethylflavone-8-carboxamide

Using a solution of 3-ethylflavone-8-carboxylic acid chloride (prepared from 2.0 g of 3-ethylflavone-8-carboxylic acid and 1.62 g of thionyl chloride) in 30 ml of benzene and 0.80 g of 2-(diethylamino-1-methyl)ethylamine, the same procedure as that described in Example 1 was performed to give 1.83 g of colorless crystals, which were recrystallized from isopropyl ether as colorless needles, m.p. 117.5°-118° C.

| Elemental analysis for $C_{25}H_{30}N_2O_3$ | C | H | N |
|---|---|---|---|
| Calcd. (%) | 73.86 | 7.44 | 6.89 |
| Found (%) | 74.05 | 7.53 | 6.88 |

EXAMPLE 28

N-(2-Diethylaminopropyl)-3-methylflavone-8-carboxamide

To a solution of 1.50 g of 3-methylflavone-8-carboxylic acid chloride in 30 ml of benzene were added 0.59 g of 2-diethylaminopropylamine and the mixture stirred for 50 minutes at room temperature. To the reaction mixture was added aqueous HCl solution and the mixture was shaken. The water layer and the precipitate were separated from the organic layer and made alkaline with potassium carbonate, then extracted with chloroform. The extract was washed with water, dried and evaporated to give 0.70 g yellow liquid. In conventional manner the compound was converted to the fumarate, which was recrystallized from ethanol as pale reddish plastes, m.p. 156.5°-158.5° C.

| Elemental analysis for $C_{24}H_{28}N_2O_3.C_4H_4O_4$ | C | H | N |
|---|---|---|---|
| Calcd. (%) | 66.13 | 6.34 | 5.51 |
| Found (%) | 66.28 | 6.42 | 5.52 |

EXAMPLE 29

N-[2-(1-Piperidyl)propyl]-3-methylflavone-8-carboxamide (a) To a solution of 3.40 g of 3-methylflavone-8-carboxylic acid chloride in 110 ml of benzene were added 1.46 g of 2-(1-piperidyl)propylamine and the mixture refluxed for 1.5 hours. The reaction mixture was treated in the same manner as in Example 5 to give 3.39 g of colorless crystals, which were recrystallized from ethyl acetate as colorless needles, m.p. 106.5°-108.5° C.

| Elemental analysis for $C_{25}H_{28}N_2O_3$ | C | H | N |
|---|---|---|---|
| Calcd. (%) | 74.23 | 6.98 | 6.93 |
| Found (%) | 74.32 | 6.95 | 6.86 |

In conventional manner, the compound was converted to the fumarate, which was recrystallized from a mixture of ethanol and acetone as colorless needles, m.p. 145°-148° C.

| Elemental analysis for $C_{25}H_{28}N_2O_3.C_4H_4O_4$ | C | H | N |
|---|---|---|---|
| Calcd. (%) | 66.91 | 6.20 | 5.38 |
| Found (%) | 66.92 | 6.52 | 5.19 |

(b) To a solution of 4.00 g of 3-methylflavone-8-carboxylic acid and 1.98 ml of triethylamine in 74 ml of anhydrous tetrahydrofuran was added a solution of 1.50 ml of ethyl chlorocarbonate in 15 ml of anhydrous tetrahydrofuran under ice-cooling and the mixture was stirred for 1 hour. To the mixture, a solution of 2.03 g of 2-piperidinopropylamine in 20 ml of anhydrous tetrahydrofuran was added and the mixture was stirred for 1.5 hours under ice-cooling and further at room temperature for 16 hours. The reaction mixture was treated by the same procedure as in Examples 3(b) to give 4.15 g of colorless crystals, which were recrystallized from ethyl acetate as colorless needles, m.p. 106.5°-108.5° C.

The compound was identical with the product obtained in Example 29(a) in NMR and IR spectra, and mixed m.p.

EXAMPLE 30

N-(2-Diethylaminoethyl)-3,3'-dimethylflavone-8-carboxamide

To a solution of 3,3'-dimethylflavone-8-carboxylic acid chloride (prepared from 1.00 g of 3,3'-dimethylflavone-8-carboxylic acid and 0.50 ml of thionyl chloride) in 30 ml of benzene were added 0.36 g of N,N-dimethylaminoethylenediamine and the mixture was stirred for 2 hours at room temperature. To the mixture was added aqueous HCl solution and the mixture was shaken. The water layer was separated, and made alkaline with potassium carbonate and extracted with chloroform. The extract was washed with water, dried, and evaporated. The residue was purified by column chromatography (adsorbent: alumina, eluted with chloroform) as 0.35 g of yellow crystals, m.p. 79.5°-86° C.

EXAMPLE 31

N-(3-Piperidinopropyl)-3,3'-dimethylflavone-8-carboxamide

To a solution of 3,3'-dimethylflavone-8-carboxylic acid chloride (prepared from 1.00 g of 3,3'-dimethylflavone-8-carboxylic acid and 0.50 ml of thionyl chloride) in 30 ml of benzene were added 0.44 g of 3-piperidinopropylamine and the mixture was stirred for 2 hours at room temperature. To the mixture was added aqueous HCl soluction and the mixture was shaken. The water layer was separated and made alkaline with potassium carbonate and extracted with chloroform. The extract was washed with water, dried, and evaporated, and to the residue was added isopropyl ether. The precipitate was filtered to give 0.80 g of reddish brown crystals, which were recrystallized from a mixture of acetone and water as colorless needles, m.p. 112°-114° C.

| Elemental analysis for $C_{26}H_{30}N_2O_3$ | C | H | N |
|---|---|---|---|
| Calcd. (%) | 74.61 | 7.22 | 6.69 |
| Found (%) | 74.24 | 7.17 | 6.65 |

EXAMPLE 32

N-(2-Diethylaminoethyl-3,4'-dimethylflavone-8-carboxamide

Using a solution of 3,4'-dimethylflavone-8-carboxylic acid chloride (prepared from 1.00 g of 3,4'-dimethylflavone-8-carboxylic acid and 0.50 ml of thionyl chloride) in 30 ml of benzene and 0.36 g of N,N-diethylethylenediamine, the same procedure as in Example 31 was performed to give 0.91 g of pale yellow crystals, m.p. 108°-113.5° C.

In conventional manner, the compound was converted to the fumarate, which was recrystallized from ethanol as colorless prisms, m.p. 150°-151° C.

| Elemental analysis for $C_{24}H_{28}N_2O_3.C_4H_4O_4$ | C | H | N |
|---|---|---|---|
| Calcd. (%) | 66.13 | 6.34 | 5.51 |
| Found (%) | 66.13 | 6.38 | 5.46 |

EXAMPLE 33

N-[(2-Dimethylamino-1-methyl)ethyl]-3,4'-dimethylflavone-8-carboxamide

The same procedure as in Example 31 was performed using 0.31 g of (2-dimethylamino-1-methyl)ethylamine and a solution of 3,4'-dimethylflavone-8-carboxylic acid chloride (prepared from 1.00 g of 3,4'-dimethylflavone-8-carboxylic acid and 0.50 ml of thionyl chloride) in 30 ml benzene to give 0.97 g of pale yellow crystals, which were recrystallized from ethyl acetate as pale brown needles, m.p. 155°-156° C.

| Elemental analysis for $C_{23}H_{26}N_2O_3$ | | | |
|---|---|---|---|
| | C | H | N |
| Calcd. (%) | 72.99 | 6.92 | 7.40 |
| Found (%) | 72.92 | 6.77 | 7.40 |

In conventional manner, the compound was converted to the fumarate, which was recrystallized from ethanol as colorless plates, m.p. 187.5°-189.5° C.

| Elemental analysis for $C_{23}H_6N_2O_3.C_4H_4O_4$ | | | |
|---|---|---|---|
| | C | H | N |
| Calcd. (%) | 65.58 | 6.11 | 5.66 |
| Found (%) | 65.64 | 6.26 | 5.59 |

EXAMPLE 34

N-(2-Diethylaminoethyl)-3'-methoxy-3-methylflavone-8-carboxamide

The same procedure as in Example 31 was performed using 0.67 g of N,N-diethylethylenediamine and a solution of 3'-methoxy-3-methylflavone-8-carboxylic acid chloride (prepared from 2.00 g of 3'-methoxy-3-methylflavone-8-carboxylic acid and 4.72 ml of thionyl chloride) in 60 ml of benzene to give 1.36 g of yellow crystals, which were recrystallized from a mixture of ethyl acetate and isopropyl ether as colorless needles, m.p. 90.5°-91.5° C.

| Elemental analysis for $C_{24}H_{28}N_2O_3$ | | | |
|---|---|---|---|
| | C | H | N |
| Calcd. (%) | 70.57 | 6.91 | 6.86 |
| Found (%) | 70.34 | 6.71 | 6.72 |

EXAMPLE 35

N-(2-Piperidinopropyl)-3'-methoxy-3-methylflavone-8-carboxamide

The same procedure as in Example 31 was performed using 0.41 g of 2-piperidinopropylamine and a solution of 3'-methoxy-3-methylflavone-8-carboxylic acid chloride (prepared from 1.00 g 3'-methoxy-3-methylflavone-8-carboxylic acid and 1.88 ml of thionyl chloride) in 30 ml of benzene to give 0.61 g of pale yellow crystals, which were recrystallized from a mixture of ethyl acetate and isopropyl ether as colorless needles m.p. 95°-97° C.

| Elemental analysis for $C_{26}H_{30}N_2O_4$ | | | |
|---|---|---|---|
| | C | H | N |
| Calcd. (%) | 71.87 | 6.96 | 6.45 |
| Found (%) | 71.80 | 6.91 | 6.47 |

EXAMPLE 36

N-(2-Diethylaminoethyl)-4'-methoxy-3-methylflavone-8-carboxamide (a) The same procedure as in Example 31 was performed using 0.34 g of N,N-diethylethylenediamine and a solution of 4'-methoxy-3-methylflavone-8-carboxylic acid chloride (prepared from 1.00 g of 4'-methoxy-3-methylflavone-8-carboxylic acid and 0.71 ml of thionyl chloride) in 50 ml of benzene to give 1.05 g of pale yellow crystals, which were recrystallized from ethyl acetate as colorless needles m.p. 125.5°-127° C.

| Elemental analysis for $C_{24}H_{28}N_2O_4$ | | | |
|---|---|---|---|
| | C | H | N |
| Calcd. (%) | 70.57 | 6.91 | 6.86 |
| Found (%) | 70.42 | 7.04 | 6.85 |

(b) To a solution of 6.00 g of 4'-methoxy-3-methylflavone-8-carboxylic acid and 2.70 ml of triethylamine in 70 ml of anhydrous tetrahydrofuran was added a solution of 2.03 ml of ethyl chlorocarbonate in 10 ml of anhydrous tetrahydrofuran and the mixture was stirred for 1 hour under ice-cooling. To the reaction mixture was added a solution of 2.25 g of N,N-diethylethylenediamine in 10 ml of anhydrous tetrahydrofuran and the mixture was stirred for 1.5 hours under ice-cooling and further 16 hours at room temperature. The reaction mixture was treated by the same procedure as in Example 3(b), to give 3.55 g of pale yellow crystals, which were recrystallized from ethyl acetate as colorless needles, m.p. 125.5°-127° C. This compound was identical with the product obtained in Example 36(a) in NMR and IR spectra, and mixed m.p.

EXAMPLE 37

N-(2-Diethylaminoethyl)-3'-chloro-3-methylflavone-8-carboxamide

To a solution of 3'-chloro-3-methylflavone-8-carboxylic acid chloride (prepared from 1.00 g of 3'-chloro-3-methylflavone-8-carboxylic acid and 0.46 ml of thionyl chloride) in 40 ml of benzene were added 0.33 g of N,N-diethylethylenediamine and the solution was stirred for 80 minutes at room temperature. To the reaction mixture was added aqueous HCl solution and shaken. The water layer was separated and made alkaline with potassium carbonate and extracted with chloroform. The extract was washed with water, dried, and evaporated. The residue was purified by column chromatography (adsorbent: silica gel, eluted with chloroform and chloroform containing 1% of methanol) to give 0.39 g of yellow crystals, which were recrystallized from isopropyl ether as colorless plates, m.p. 116°-117° C.

| Elemental analysis for $C_{23}H_{25}ClN_2O_3$ | | | |
|---|---|---|---|
| | C | H | N |
| Calcd. (%) | 66.90 | 6.10 | 6.78 |
| Found (%) | 66.67 | 6.18 | 6.56 |

EXAMPLE 38

N-(2-Diethylaminoethyl)-3'-methylflavone-8-carboxamide

The same procedure as in Example 31 was performed using 0.37 g of N,N-diethylethylenediamine and a solution of 3'-methylflavone-8-carboxylic acid chloride (prepared from 1.00 g of 3'-methylflavone-8-carboxylic acid and 0.52 ml of thionyl chloride) in 40 ml of benzene to give 0.9 g of pale yellow crystals, which were recrystallized from ethyl acetate as colorless needles, m.p. 160.5°-162.5° C.

| Elemental analysis for $C_{23}H_{26}N_2O_3$ | | | |
|---|---|---|---|
| | C | H | N |
| Calcd. (%) | 72.99 | 6.92 | 7.40 |
| Found (%) | 72.59 | 6.85 | 7.28 |

In conventional manner, the compound was converted to the fumarate, which was recrystallized from ethanol as colorless needles, m.p. 167°–168.5° C.

| Elemental analysis for $C_{23}H_{26}N_2O_3 \cdot C_4H_4O_4$ | | | |
|---|---|---|---|
| | C | H | N |
| Calcd. (%) | 65.58 | 6.11 | 5.66 |
| Found (%) | 65.88 | 6.16 | 5.73 |

EXAMPLE 39

N-[(2-Dimethylamino-1-methyl)ethyl]-3'-methylflavone-8-carboxamide

The same procedure as in Example 31 was performed using 0.33 g of (2-dimethylamino-1-methyl)-ethylamine and a solution of 3'-methylflavone-8-carboxylic acid chloride (prepared from 1.00 g of 3'-methylflavone-8-carboxylic acid and 0.52 ml of a thionyl chloride) in 40 ml of benzene to give 1.01 g of pale yellow crystals, which were recrystallized from ethyl acetate as colorless needles, m.p. 156°–157.5° C.

| Elemental analysis for $C_{22}H_{24}N_2O_3$ | | | |
|---|---|---|---|
| | C | H | N |
| Calcd. (%) | 72.51 | 6.64 | 7.69 |
| Found (%) | 72.61 | 6.64 | 7.69 |

In conventional manner, the compound was converted to the fumarate, which was recrystallized from methanol to give colorless needles, m.p. 185°–187.5° C.

| Elemental analysis for $C_{22}H_{24}N_2O_3 \cdot C_4H_4O_4 \cdot \frac{1}{4}H_2O$ | | | |
|---|---|---|---|
| | C | H | N |
| Calcd. (%) | 64.39 | 5.92 | 5.78 |
| Found (%) | 64.28 | 5.92 | 5.60 |

EXAMPLE 40

N-(2-Diethylaminoethyl)-4'-methylflavone-8-carboxamide

The same procedure as in Example 31 was performed using 0.37 g of N,N-diethylethylenediamine and a solution of 4'-methylflavone-8-carboxylic acid chloride (prepared from 1.00 g of 4'-methylflavone-8-carboxylic acid and 0.60 ml of thionyl chloride) in 30 ml of benzene to give 0.96 g of brown crystals.

EXAMPLE 41

N-(2-Diethylaminoethyl)-3'-methoxyflavone-8-carboxamide

The same procedure as in Example 31 was performed using 0.35 g of N,N-diethylethylenediamine and a solution of 3'-methoxyflavone-8-carboxylic acid chloride (prepared from 1.00 g of 3'-methoxyflavone-8-carboxylic acid and 0.49 ml of thionyl chloride) in 30 ml of benzene to give 0.95 g of pale brown crystals, which were recrystallized from ethyl acetate as colorless needles, m.p. 151.5°–152°-5° C.

| Elemental analysis for $C_{23}H_{26}N_2O_4$ | | | |
|---|---|---|---|
| | C | H | N |
| Calcd. (%) | 70.03 | 6.64 | 7.10 |
| Found (%) | 70.03 | 6.63 | 6.96 |

In conventional manner, the compound was converted to the fumarate, which was recrystallized from ethanol as colorless needles, m.p. 172°–173° C.

| Elemental analysis for $C_{23}H_{26}N_2O_4 \cdot C_4H_4O_4$ | | | |
|---|---|---|---|
| | C | H | N |
| Calcd. (%) | 63.52 | 5.92 | 5.49 |
| Found (%) | 63.42 | 6.20 | 5.45 |

EXAMPLE 42

N-(2-Piperidinopropyl)-3'-methoxyflavone-8-carboxamide

The same procedure as in Example 31 was performed using 0.43 g of 2-piperidinopropylamine and solution of 3'-methoxyflavone-8-carboxylic acid chloride (prepared from 3'-methoxyflavone-8-carboxylic acid and 0.49 ml of thionyl chloride) in 30 ml of benzene to give 1.09 g of pale yellow crystals, which were recrystallized from ethanol as pale brown plates, m.p. 163°–164° C.

| Elemental analysis for $C_{25}H_{28}N_2O_4$ | | | |
|---|---|---|---|
| | C | H | N |
| Calcd. (%) | 71.41 | 6.71 | 6.66 |
| Found (%) | 71.36 | 6.82 | 6.58 |

In conventional manner, the compound was converted to the fumarate, which was recrystallized from methanol as pale brown needles, m.p. 175°–176.5° C. (decomp.).

| Elemental analysis for $C_{25}H_{28}N_2O_4 \cdot C_4H_4O_4 \cdot \frac{1}{2}H_2O$ | | | |
|---|---|---|---|
| | C | H | N |
| Calcd. (%) | 63.84 | 6.10 | 5.13 |
| Found (%) | 63.94 | 6.02 | 5.10 |

EXAMPLE 43

N-(2-Diethylaminoethyl)-4'-methoxyflavone-8-carboxamide

The same procedure as in Example 31 was performed using 0.35 g of N,N-diethylethylenediamine and a solution of 4'-methoxyflavone-8-carboxylic acid chloride (prepared from 1.00 g of 4'-methoxyflavone-8-carboxylic acid and 0.74 ml of thionyl chloride) in 30 ml of benzene to give 0.91 g of pale brown crystals, m.p. 156.5°–158.5° C.

In conventional manner, the compound was converted to the fumarate, which was recrystallized from ethanol as colorless plates, m.p. 151°–154° C.

| Elemental analysis for $C_{23}H_{26}N_2O_4 \cdot C_4H_4O_4 \cdot H_2O$ | | | |
|---|---|---|---|
| | C | H | N |
| Calcd. (%) | 61.36 | 6.10 | 5.30 |

-continued

| Elemental analysis for $C_{23}H_{26}N_2O_4.C_4H_4O_4.H_2O$ | C | H | N |
|---|---|---|---|
| Found (%) | 61.26 | 5.89 | 5.37 |

EXAMPLE 44

N-(2-Piperidinopropyl)-4'-methoxyflavone-8-carboxamide

To a suspension of 4'-methoxyflavone-8-carboxylic acid chloride (prepared from 3.00 g of 4'-methoxyflavone-8-carboxylic acid and 1.48 ml of thionyl chloride) in 60 ml of benzene were added 1.30 g of 2-piperidinopropylamine and the mixture was stirred for 40 minutes at room temperature and refluxed for 1 hour. The reaction mixture was treated in the same manner as described in Example 5 to give 1.80 g of pale brown crystals, which were recrystallized from ethanol as colorless needles, m.p. 171.5°-174.5° C.

| Elemental analysis for $C_{25}H_{28}N_2O_4$ | C | H | N |
|---|---|---|---|
| Calcd. (%) | 71.41 | 6.71 | 6.66 |
| Found (%) | 71.34 | 6.74 | 6.50 |

In conventional manner, the compound was converted to the fumarate, which was recrystallized from methanol as colorless needles, m.p. 216°-219° C. (decomp.).

| Elemental analysis for $C_{25}H_{28}N_2O_4.C_4H_4O_4$ | C | H | N |
|---|---|---|---|
| Calcd. (%) | 64.91 | 6.01 | 5.22 |
| Found (%) | 65.01 | 5.87 | 5.11 |

EXAMPLE 45

N-(2-Diethylaminoethyl)-3'-chloroflavone-8-carboxamide

The same procedure as in Example 31 was performed using 0.35 g of N,N-diethylethylenediamine and a solution of 3'-chloroflavone-8-carboxylic acid chloride (prepared from 1.00 g of 3'-chloroflavone-8-carboxylic acid and 0.73 ml of thionyl chloride) in 30 ml of benzene to give 1.03 g of pale brown crystals. In conventional manner, the compound was converted to the fumarate, which was recrystallized from ethanol as colorless needles, m.p. 186°-188° C.

| Elemental analysis for $C_{22}H_{23}ClN_2O_3.C_4H_4O_4.\frac{1}{2}H_2O$ | C | H | N |
|---|---|---|---|
| Calcd. (%) | 59.60 | 5.39 | 5.35 |
| Found (%) | 59.58 | 5.48 | 5.37 |

EXAMPLE 46

N-(3-Piperidinopropyl)-3'-chloroflavone-8-carboxamide

The same procedure as in Example 31 was performed employing 0.43 g of 3-piperidinopropylamine and 3'-chloroflavone-8-carboxylic acid chloride (prepared from 1.00 g of 3'-chloroflavone-8-carboxylic acid and 0.73 ml of thionyl chloride) in 30 ml of benzene to give 1.14 g of pale brown crystals.

In conventional manner, the compound was converted to the fumarate, which was recrystallized from a mixture of ethanol and ether as pale brown needles, m.p. 151.5°-153.5° C.

| Elemental analysis for $C_{24}H_{25}ClN_2O_3.C_4H_4O_4$ | C | H | N |
|---|---|---|---|
| Calcd. (%) | 62.16 | 5.40 | 5.18 |
| Found (%) | 62.16 | 5.38 | 5.22 |

EXAMPLE 47

N-(2-Diethylaminoethyl)-4'-chloroflavone-8-carboxamide

The same procedure as in Example 31 was performed employing 0.35 g of N,N-diethylethylenediamine and a solution of 4'-chloroflavone-8-carboxylic acid chloride (prepared from 1.00 g of 4'-chloroflavone-8-carboxylic acid and 0.73 ml of thionyl chloride) in 40 ml of benzene to give 0.83 g of pale brown crystals, which were recrystallized from ethyl acetate as colorless needles, m.p. 181.5°-184° C.

| Elemental analysis for $C_2H_{23}ClN_2O_3$ | C | H | N |
|---|---|---|---|
| Calcd. (%) | 66.24 | 5.81 | 7.02 |
| Found (%) | 66.08 | 5.70 | 7.04 |

In conventional manner, the compound was converted to the fumarate, which was recrystallized from methanol as pale yellow needles, m.p. 174.5°-176° C.

| Elemental analysis for $C_{22}H_{23}ClN_2O_3.C_4H_4O_4.\frac{1}{2}H_2O$ | C | H | N |
|---|---|---|---|
| Calcd. (%) | 59.60 | 5.39 | 5.35 |
| Found (%) | 59.72 | 5.45 | 5.38 |

EXAMPLE 48

N-[(2-Dimethylamino-1-methyl)ethyl]-4'-chloroflavone-8-carboxamide

The same procedure as in Example 31 was performed employing 0.31 g of (2-dimethylamino-1-methyl)-ethylamine and a solution of 4'-chloroflavone-8-carboxylic acid chloride (prepared from 1.00 g of 4'-chloroflavone-8-carboxylic acid and 0.73 ml of thionyl chloride) in 40 ml of benzene to give 0.80 g of pale brown crystals, which were recrystallized from ethyl acetate as colorless needles, m.p. 215.5°-217° C.

| Elemental analysis for $C_{21}H_{21}ClN_2O_3$ | C | H | N |
|---|---|---|---|
| Calcd. (%) | 65.54 | 5.50 | 7.28 |
| Found (%) | 65.19 | 5.54 | 7.17 |

In conventional manner, the compound was converted to the fumarate, which was recrystallized from methanol as pale yellow needles, m.p. 199.5°-203° C.

| Elemental analysis for $C_{21}H_{21}ClN_2O_3.C_4H_4O_4.H_2O$ | C | H | N |
|---|---|---|---|
| Calcd. (%) | 57.86 | 5.24 | 5.40 |
| Found (%) | 57.59 | 5.23 | 5.40 |

EXAMPLE 49

N-(2-Diethylaminoethyl)-4'-fluoroflavone-8-carboxamide

The same procedure as in Example 31 was performed employing 0.37 g of N,N-diethylethylenediamine and a solution of 4'-fluoroflavone-8-carboxylic acid chloride (prepared from 1.00 g of 4'-fluoroflavone-8-carboxylic acid and 0.77 ml of thionyl chloride) in 30 ml of benzene to give 0.90 g of pale brown crystals, which were recrystallized from ethanol as pale yellow needles, m.p. 173.5°-175° C.

| Elemental analysis for $C_{22}H_{23}FN_2O_3$ | C | H | N |
|---|---|---|---|
| Calcd. (%) | 69.09 | 6.06 | 7.33 |
| Found (%) | 69.13 | 5.79 | 7.33 |

In conventional manner, the compound was converted to the fumarate, which was recrystallized from ethanol as pale brown needles, m.p. 181°-183.5° C.

| Elemental analysis for $C_{22}H_{23}FN_2O_3.C_4H_4O_4.\frac{1}{2}H_2O$ | C | H | N |
|---|---|---|---|
| Calcd. (%) | 61.53 | 5.56 | 5.52 |
| Found (%) | 61.33 | 5.90 | 5.21 |

EXAMPLE 50

N-(2-Piperidinopropyl)-4'-fluoroflavone-8-carboxamide

The same procedure as in Example 31 was performed employing 0.45 g of 2-piperidinopropylamine and a solution of 4'-fluoroflavone-8-carboxylic acid chloride (prepared from 1.00 g of 4'-fluoroflavone-8-carboxylic acid and 0.77 ml of thionyl chloride) in 30 ml of benzene to give 0.9 g of pale brown crystals, which were recrystallized from ethyl acetate as colorless needles, m.p. 177.5°-179.5° C.

| Elemental analysis for $C_{24}H_{25}FN_2O_3$ | C | H | N |
|---|---|---|---|
| Calcd. (%) | 70.57 | 6.17 | 6.86 |
| Found (%) | 70.47 | 6.19 | 6.89 |

In conventional manner, the compound was converted to the fumarate, which was recrystallized from methanol as colorless needles, m.p. 233°-236° C.

| Elemental analysis for $C_{24}H_{25}FN_2O_3.C_4H_4O_4$ | C | H | N |
|---|---|---|---|
| Calcd. (%) | 64.11 | 5.57 | 5.34 |
| Found (%) | 64.12 | 5.52 | 5.36 |

EXAMPLE 51

N-(2-Diethylaminoethyl)-4'-nitroflavone-8-carboxamide

The same procedure as in Example 31 was performed employing 0.34 g of N,N-diethylethylenediamine and 4'-nitroflavone-8-carboxylic acid chloride (prepared from 1.00 g of 4'-nitroflavone-8-carboxylic acid and 1.40 ml of thionyl chloride) in 30 ml of benzene to give 0.78 g of yellow crystals, which were recrystallized from methanol as yellowish brown crystals, m.p. 207°-209° C.

| Elemental analysis for $C_{22}H_{23}N_3O_5$ | C | H | N |
|---|---|---|---|
| Calcd. (%) | 64.54 | 5.66 | 10.26 |
| Found (%) | 64.50 | 5.40 | 10.06 |

EXAMPLE 52

N-(3-Piperidinopropyl)-3'-chloro-3-methylflavone-8-carboxamide

The same procedure as in Example 31 was performed employing 0.41 g of 3-piperidinopropylamine and a solution of 3'-chloro-3-methylflavone-8-carboxylic acid chloride (prepared from 1.00 g of 3'-chloro-3-methylflavone-8-carboxylic acid and 1.39 ml of thionyl chloride) in 30 ml of benzene to give 1.19 g of pale brown crystals, which were recrystallized from ethyl acetate as colorless needles, m.p. 128°-131° C.

| Elemental analysis for $C_{25}H_{27}ClN_2O_3$ | C | H | N |
|---|---|---|---|
| Calcd. (%) | 68.41 | 6.20 | 6.38 |
| Found (%) | 68.41 | 6.23 | 6.17 |

In conventional manner, the compound was converted to the fumarate, which was recrystallized from ethanol as pale brown needles, m.p. 124°-125.5° C.

| Elemental analysis for $C_{25}H_{27}ClN_2O_3.C_4H_4O_4$ | C | H | N |
|---|---|---|---|
| Calcd. (%) | 62.76 | 5.63 | 5.05 |
| Found (%) | 62.75 | 5.71 | 4.89 |

We claim:

1. N-substituted flavone-8-carboxamide represented by the formula (I):

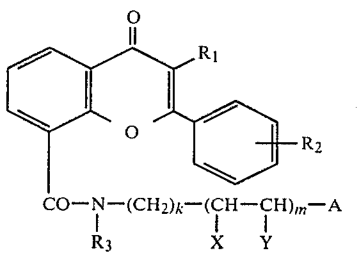

(I)

wherein $R_1$ represents a hydrogen atom, a methyl group or an ethyl group; $R_2$ represents a hydrogen atom, a lower alkyl group, a lower alkoxyl group, a hologen atom or a nitro group; $R_3$ represents a hydrogen atom or a lower alkyl group; k represents 0, 1, 2, or 3; m represents 0 or 1; X and Y, which must be different, represent a hydrogen atom or a methyl group; A represents an amino group having the formula

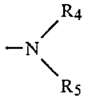

or

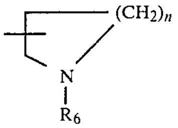

wherein, $R_4$ and $R_5$, which may be the same or different, represent a lower alkyl group or a cyclic amino group together with the nitrogen atom and with or without an oxygen atom to constitute a piperidino, pyrrolidino or morpholino group; $R_6$ represents a lower alkyl group and n represents 2 or 3; and pharmaceutically acceptable acid addition salts thereof.

2. N-substituted flavone-8-carboxamide of claim 1 represented by the formula:

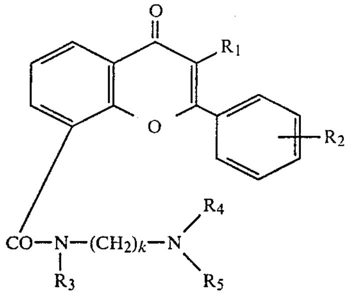

wherein $R_1$, $R_2$, $R_3$, and the group

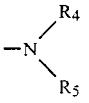

have the same meanings as defined in claim 1 and k means 2 or 3.

3. N-substituted flavone-8-carboxamide of claim 1 represented by the formula:

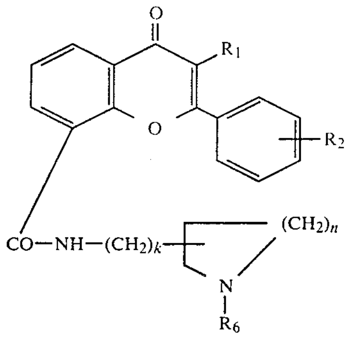

wherein $R_1$, $R_2$ and the group

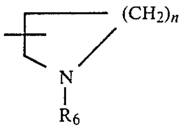

have the same meanings as defined in claim 1 and k means 0, 1 or 2.

4. N-substituted flavone-8-carboxamide of claim 1 represented by the formula:

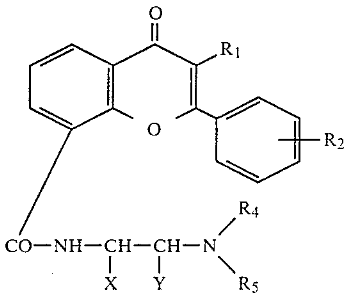

wherein $R_1$, $R_2$, X, Y, and the group

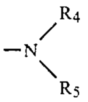

have the same meanings as defined in claim 1.

5. N-substituted flavone-8-carboxamide of claim 1 represented by the formula:

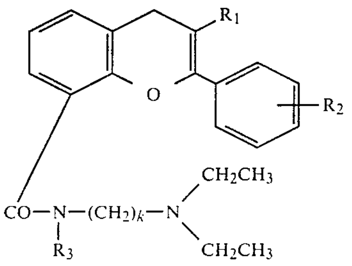

wherein $R_1$, $R_2$ and $R_3$ have the same meanings as defined in claim 1 and k means 2 or 3.

6. N-substituted flavone-8-carboxamide of claim 1 represented by the formula:

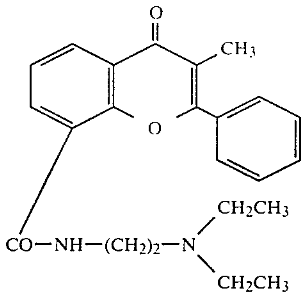

7. N-substituted flavone-8-carboxamide of claim 1 represented by the formula:

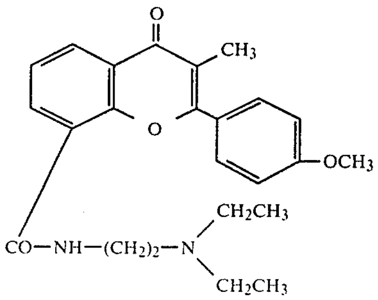

8. N-substituted flavone-8-carboxamide of claim 1 represented by the formula:

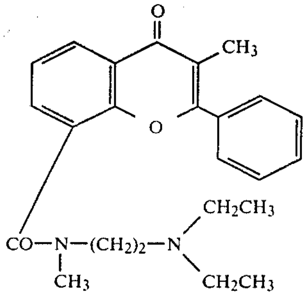

9. N-substituted flavone-8-carboxamide of claim 1 represented by the formula:

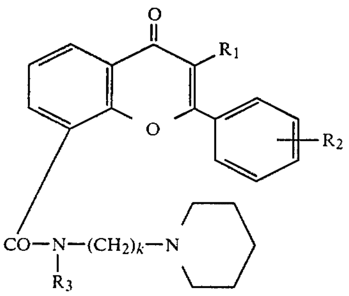

wherein $R_1$, $R_2$ and $R_3$ have the same meanings as defined in claim 1 and k means 2 or 3.

10. N-substituted flavone-8-carboxamide of claim 1 represented by the formula:

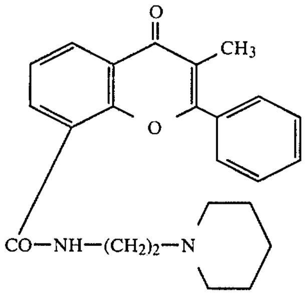

11. N-substituted flavone-8-carboxamide of claim 1 represented by the formula:

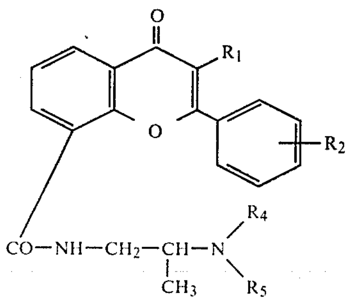

wherein $R_1$, $R_2$ and the group

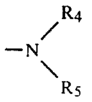

have the same meanings as defined in claim 1.

12. N-substituted flavone-8-carboxamide of claim 1 represented by the formula:

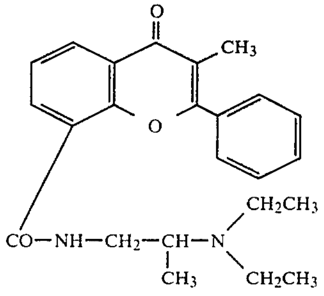

13. N-substituted flavone-8-carboxamide of claim 1 represented by the formula:

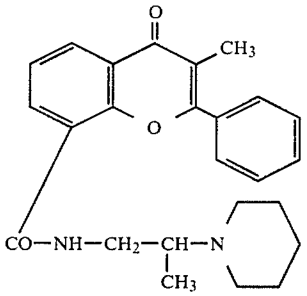

14. N-substituted flavone-8-carboxamide of claim 1 represented by the formula:

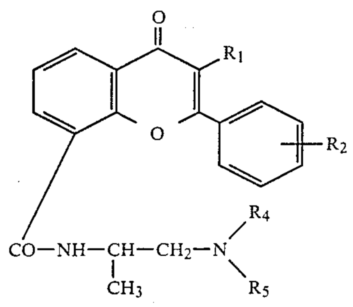

wherein $R_1$, $R_2$ and the group

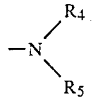

have the same meanings as defined in claim 1.

15. N-substituted flavone-8-carboxamide of claim 1 represented by the formula:

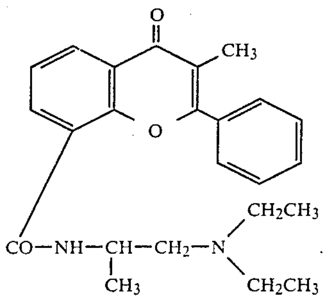

16. A pharmaceutical composition, suitable for use in treating an impediment to micturition, comprising a compound of claim 1 in an amount effective for such purpose in associating with a pharmaceutically-acceptable carrier.

17. A method for the treatment of a subject in need of elimination of an impediment to micturition, comprising the step of administering to a said subject an amount of a compound of claim 1 which is effective for such purpose.

18. A method of claim 17 wherein the compound is administered in association with a pharmaceutically-acceptable carrier.

* * * * *

UNITED STATES PATENT AND TRADEMARK OFFICE

CERTIFICATE OF CORRECTION

PATENT NO. : 4,525,356

DATED : June 25, 1985

INVENTOR(S) : Yasuo Itho, Hideo Kato, Nobuo Ogawa, Kagari Yamagishi, Eiichi Koshinaka and Kazuya Mitani It is certified that error appears in the above-identified patent and that said Letters Patent is hereby corrected as shown below:

Col. 2, line 17; "are" should read -- art --
Col. 6, line 55; "whereing" should read -- wherein --
Col. 7, line 41; "supression" should read -- suppression --
Col. 7, line 48; "supression" should read -- suppression --
Col. 9, line 38; "Supression" should read -- Suppression --
Col. 9, line 54; insert -- a -- before "balloon"
Col. 9, line 67; "result as" should read -- results are --
Col. 10, line 2; "Supression" should read -- Suppression --
Col. 10, line 15; "supressing" should read -- suppressing --
Col. 12, line 45; delete "a"
Col. 14, line 20; "evaorated" should read -- evaporated --
Col. 15, line 27; "wre" should read -- were --
Col. 16, line 9; "stireed" should read -- stirred --
Col. 17, lines 64 & 65; "-crboxamide" should read -- -carboxamide --
Col. 34, line 67; "hologen" should read -- halogen --
Col. 26, line 19; "soluction" should read -- solution --

UNITED STATES PATENT AND TRADEMARK OFFICE

CERTIFICATE OF CORRECTION

PATENT NO. : 4,525,356

DATED : June 25, 1985

INVENTOR(S) : Yasuo Itho, Hideo Kato, Nobuo Ogawa, Kagari Yamagishi, Eiichi Koshinaka and Kazuya Mitani It is certified that error appears in the above-identified patent and that said Letters Patent is hereby corrected as shown below:

Col. 1, line 27; "alkoxy" should read -- alkoxyl --
Col. 2, line 54; "atoms" should read -- atom --
Col. 4, line 44; "alkoxy" should read -- alkoxyl --
Col. 7, line 26; "roam" should read -- room --
Col. 13, line 34; "is" should read -- was --
Col. 14, line 61; "alkalline" should read -- alkaline --
Col. 15, line 38; "ethanolether" should read -- ethanol - ether --
Col. 22, line 66; "are" should read -- were --
Col. 25, line 4; insert a comma -- , -- after "manner"
Col. 25, line 6; "plastes" should read -- plates --
Col. 25, line 66; "-dimethyl-" should read -- -diethyl- --

Col. 29, line 26; delete "a"
Col. 36, the formula in claim 5;

" 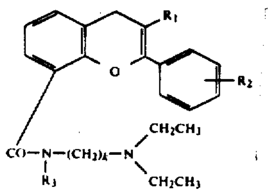 " should read -- 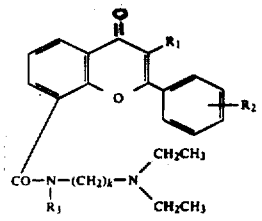 --

Signed and Sealed this

*Thirty-first* Day of *December 1985*

[SEAL]

*Attest:*

DONALD J. QUIGG

*Attesting Officer* *Commissioner of Patents and Trademarks*